(12) United States Patent
Bishopric et al.

(10) Patent No.: US 9,248,144 B2
(45) Date of Patent: Feb. 2, 2016

(54) COMPOSITIONS, KITS AND METHODS FOR TREATMENT OF CARDIOVASCULAR, IMMUNOLOGICAL AND INFLAMMATORY DISEASES

(75) Inventors: Nanette Bishopric, Coral Gables, FL (US); Jing Liu, Miami, FL (US); Salil Sharma, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

(21) Appl. No.: 13/884,060

(22) PCT Filed: Nov. 11, 2011

(86) PCT No.: PCT/US2011/060309
§ 371 (c)(1),
(2), (4) Date: May 23, 2013

(87) PCT Pub. No.: WO2012/065027
PCT Pub. Date: May 18, 2012

(65) Prior Publication Data
US 2013/0236437 A1    Sep. 12, 2013

Related U.S. Application Data

(60) Provisional application No. 61/412,480, filed on Nov. 11, 2010.

(51) Int. Cl.
*A61K 48/00* (2006.01)
*A61K 31/7088* (2006.01)
*C12N 15/113* (2010.01)
*C12Q 1/68* (2006.01)

(52) U.S. Cl.
CPC .......... *A61K 31/7088* (2013.01); *C12N 15/113* (2013.01); *C12Q 1/6876* (2013.01); *C12N 2310/113* (2013.01); *C12N 2310/3231* (2013.01)

(58) Field of Classification Search
USPC ............... 424/93.21; 435/1.1, 6.11, 325, 377, 435/455; 514/44; 536/23.1, 24.5
See application file for complete search history.

(56) References Cited

U.S. PATENT DOCUMENTS

2009/0004668 A1*  1/2009  Chen et al. ............. 435/6
2010/0173288 A1*  7/2010  Zhang et al. ............ 435/6
2010/0202973 A1   8/2010  Pivarcsi et al.

FOREIGN PATENT DOCUMENTS

| WO | 2007000668 A2 | 1/2007 |
|---|---|---|
| WO | 2007112753 A2 | 10/2007 |
| WO | 2008014008 | 1/2008 |
| WO | 2008042231 A2 | 4/2008 |
| WO | 2008068046 | 6/2008 |
| WO | 2008073919 | 6/2008 |
| WO | 2009097136 A1 | 8/2009 |
| WO | 2009108866 A2 | 9/2009 |
| WO | 2009137807 A2 | 11/2009 |
| WO | 2010126370 A2 | 11/2010 |

OTHER PUBLICATIONS

Doench et al, Genes & Development, vol. 17, pp. 438-442, (2003).*
Opalinska et al, Nature Rev., vol. 1, pp. 503-514 (2002).*
Jang et al, Expert Rev. Medical Devices, vol. 1, No. 1, pp. 127-138 (2004).*
Paroo et al, Trends in Biotech, vol. 22, No. 8, pp. 390-394 (2004).*
Fontana et al., "MicroRNAs 17-5p-20a-106a control monocytopoiesis through AML1 targeting and M-CSF receptor upregulation", Nature Cell Biology (Jul. 1, 2007) 9(1): 775-787.
Sharma, "MicroRNAs as effectors for acetyltransferase p300 in cardiac hypertrophy", University of Miami Thesis (Dec. 8, 2011). Retrieved on Nov. 6, 2014, from http://scholarlyrepository.miami.edu/cgi/viewcontent.cgi?article=1689&context=oadissertations.
Sharma et al., "Repression of MiR-142 by p300 and MAPK is required for survival signaling via gp130 during adaptive hypertrophy", EMBO Molecular Medicine (Jul. 24, 2012) 4(7): 617-632.
Shehadeh et al., "A microRNA-20a-p300 circuit in cardiac myocytes and cardiac stem cells regulates compensatory angiogenesis during cardiac hypertrophy", Circulation (Nov. 13, 2010) 122(21) Suppl. S: A13758.
Shehadeh et al., "Loss of miR-20a promotes vasculogenesis of cardiac stem cells", Journal of the American College of Cardiology (Mar. 28, 2009) 53(10) Suppl 1: A457.
Shehadeh et al., "MicroRNA-20a constrains p300-driven myocardial angiogenic transcription by direct targeting of p300", PLOS One (Nov. 13, 2013) 8(11): E79133. (13 pages).
Shehadeh et al., "Regulation of compensatory angiogenesis during cardiac hypertrophy by a p300-miR-17 similar to 92 feedback loop", Circulation (Nov. 2009) 120(18) Suppl. 2: S583.
Shehadeh et al., "Regulation of compensatory angiogenesis during cardiac hypertrophy by a p300-miR-17~92 feedback loop", Arteriosclerosis, Thrombosis, and Vascular Biology (Apr. 29, 2009) 29(7): P451.

(Continued)

*Primary Examiner* — Jane Zara
(74) *Attorney, Agent, or Firm* — Novak Druce Conolly Bove + Quigg LLP

(57) ABSTRACT

Compositions, kits, cells and methods for treating cardiovascular (e.g., myocardial ischemia and heart failure), immunological, and inflammatory diseases or disorders involve the use of the mature and precursor sequences of microRNAs 142-5p, 142-3p, 17-5p, 17-3p, 374, and 20a, and of antisense molecules complementary to these sequences, to manipulate processes relevant to, for example, the cardiac response to stress, including survival signaling, angiogenesis, stem cell differentiation along muscle or vascular lineages, and repression or promotion of cardiac myocyte growth. Also described are methods to treat cardiovascular, immunological and inflammatory diseases by engineering cells containing specific micro-RNAs or antagomirs against specific mRNAs. The engineered cells can then be used to treat patients with such diseases by autologous stem cell therapy.

3 Claims, 5 Drawing Sheets

(56) References Cited

OTHER PUBLICATIONS

Bonauer et al., "MicroRNA-92a controls angiogenesis and functional recovery of ischemic tissues in mice", Science (2009) 324: 1710-1713.

Doebele et al., "Members of the micro-RNA-17-92 cluster exhibit a cell-intrinsic antiangiogenic function in endothelial cells", Blood (Jun. 2010) 115(23): 4944-4950.

Shehadeh et al., "MicroRNA-20a restores cardiac function in P300 hypertrophic hearts by targeting P300-driven angiogenic program in cardiac myocytes and cardiac progenitor cells", JACC (Apr. 5, 2011) 57(14): 0406-08. (abstract only).

Shehadeh et al., "miR-17-92 cluster is involved in the angiogenic switch in cardiac hypertrophy", Retrieved on Apr. 29, 2012 from http://www.med.miami.edu/mnbws/documents/SHEHADEH.pdf (2 pages).

Voellenkle Christine et al: "MicroRNA signatures in peripheral blood mononuclear cells of chronic heart failure patients", Physiological Genomics, American-Physiological Society, US, vol. 42, No. 3, Aug. 1, 2010, pp. 420-426, DOI:10.1152/PHYSIOLGENOMICS.00211. 2009 [retrieved on May 18, 2010].

Jin Ping et al: "Differentiation of two types of mobilized peripheral blood stem cells by microRNA and eDNA expression analysis", Journal of Translational Medicine, Biomed Central, London, GB, vol. 6, No. 1, Jul. 22, 2008, p. 39.

Nishiyama Takahiko et al: "MicroRNA 142-3p Regulates Heart Development,Somitegenesis and Hematopoiesis in the Stage of Early Mesoderm Formation", Circulation, vol. 120, No. 18, Suppl. 2, Nov. 2009 , p. S605, 82nd Scientific Session of the American Heart Association; Orlando, FL, USA; Nov. 14-18, 2009. Whole document.

Sharma Salil et al: "p300 Regulates Cardiac Myocyte Growth Through MIR374-5p and MIR142-5p". Circulation vol. 122, No. 21, Suppl. S, Nov. 13, 2010-Nov. 17, 2010, p. A18465, Scientific Sessions of the American-Heart-Association on Resuscitation Science Symposium; Chicago, IL. USA; Nov. 13-17, 2010. Whole document.

Supplementary European Search Report from EP 11840237 dated Jun. 12, 2015.

\* cited by examiner

COMPOSITIONS, KITS AND METHODS FOR TREATMENT OF CARDIOVASCULAR, IMMUNOLOGICAL AND INFLAMMATORY DISEASES

CROSS REFERENCE TO RELATED APPLICATION

This is a 371 National Stage Application of International Application No. PCT/US2011/060309, filed Nov. 11, 2011, which claims priority to U.S. Provisional Application No. 61/412,480, filed Nov. 11, 2010, the entirety of which is incorporated herein by reference.

FIELD OF THE INVENTION

The invention relates generally to the fields of medicine and gene therapy. More particularly, the invention relates to compositions, cells, kits and methods for treating and preventing cardiovascular, immunological, and inflammatory diseases and disorders in a subject.

BACKGROUND

MicroRNAs (miRs) are endogenous non-coding ~22 nucleotide RNAs that affect the protein expression of their target genes by transcript cleavage or translation blockade. More than 400 microRNAs have been identified in the human genome. MicroRNAs belong to one of the largest gene families and account for ~1% of the genome. More than 30% of the human genome is estimated to be under miRNA post-transcriptional control, although the number of validated miRNA targets remains small. MicroRNAs are implicated in a number of processes including cellular differentiation, proliferation and apoptosis (e.g., cardiac and inflammatory diseases).

SUMMARY

Described herein are compositions, kits, cells and methods for treating cardiovascular (e.g., myocardial ischemia and heart failure), immunological, and inflammatory diseases or disorders based on the discovery that particular microRNAs target angiogenesis (17-5p, 17-3p, 20a), myocyte hypertrophy (374), inflammatory response (miR-142-5p and 142-3p) and immediate-early gene activation (374), all of which are involved in the initial adaptation to myocardial stress, as well as the identification of specific targets of these microRNAs, including a shared target, p300 acetyltransferase, HIF-1a, NFkB1 and 2, and alpha-actinin. The compositions and methods involve the use of the mature and precursor sequences of microRNAs 142-5p, 142-3p, 17-5p, l'7-3p, 374, and 20a, and of antisense molecules complementary to these sequences, to manipulate processes relevant to, for example, the cardiac response to stress, including survival signaling, angiogenesis, stem cell differentiation along muscle or vascular lineages, and repression or promotion of cardiac myocyte growth. Also described are methods to treat cardiovascular, immunological and inflammatory diseases by engineering cells containing specific micro-RNAs or antagomirs against specific mRNAs. The engineered cells can then be used to treat patients with such diseases, for example, by autologous stem cell therapy. Alternatively, the microRNAs or antagomirs directed against these microRNAs can be used directly as therapeutic agents. Targeting of p300 by miR-20a and the other microRNAs described herein can be used to improve cardiac function and reduce inflammatory disease in a subject (e.g., human subject).

In the experiments described herein, it was found that these microRNAs are regulated in multiple models of cardiac stress. The regulation for some of these microRNAs (miR-142 and miR-374) is temporally complex, involving an initial decrease in expression that is followed by a later upregulation. The time course is consistent with a repressive role for these microRNAs in the stress response that must be transiently relieved to permit successful adaptation to environmental insults such as ischemia/hypoxia and hemodynamic overload. The molecular structures of these microRNAs is closely conserved in human, mouse and rat. The mature and precursor miR sequences are both used in the methods of manipulating the function and expression of these microRNAs.

The function of these microRNAs can be increased through transfer of the genetic sequence of the precursor microRNA using lipid- or viral-mediated transfection, or any other method for introducing double-stranded DNA into cells. The function of these microRNAs can be reduced through transfer of an antisense singe-stranded sequence ("antagomiR") that binds and inactivates the mature miR through unknown mechanisms. Such single-stranded sequences can either be expressed from a transfected viral vector or plasmid as above. Alternatively, antagomiRs can be synthesized and stabilized against degradation by chemical modification and injected directly into the target tissue or into the venous circulation. Both approaches have been used in vitro, and the synthetic antagomiR approach was successfully used in vivo to reduce myocardial infarct size in a mouse model.

Accordingly, described herein is a composition for treating a cardiovascular disease or disorder in a subject. The composition includes a pharmaceutically acceptable carrier and an agent that decreases expression or activity of miR-20a in an amount sufficient for increasing cardiac tissue angiogenesis in the subject. The agent that decreases expression or activity of miR-20a can be an antisense molecule (e.g., an antagomiR) complementary to miR-20a. The cardiovascular disease or disorder can be one of: myocardial ischemia, cardiac failure, familial dilated cardiomyopathy, coronary artery disease, cardiac transplant rejection, hypertensive heart disease, valvular heart disease, viral myocarditis, end-stage cardiomyopathy, arrhythmogenic right ventricular dysplasia and myocardial scarring due to infarction or other injury.

Also described herein is a composition for treating a cardiovascular disease or disorder or for treating a disease or disorder associated with inflammation in a subject. The composition includes a pharmaceutically acceptable carrier and an agent that increases expression or activity of miR-20a in an amount sufficient for improving cardiac function or reducing inflammation in the subject. The disease or disorder associated with inflammation can be one of: autoimmune disorder, acute inflammation, chronic inflammation, septic shock, and organ transplant rejection. The agent that increases expression or activity of miR-20a can be a miR-20a mimic.

Further described herein is a composition for treating a cardiovascular disease or disorder in a subject. The composition includes: a pharmaceutically acceptable carrier and an agent that downregulates activity or expression of one or more of: miR-142-5p, miR-142-3p and miR-374, in an amount sufficient to promote cardiac cell survival and enhance cardiac function in the subject. The agent that reduces activity or expression of one or more of: miR-142-5p, miR-142-3p and miR-374 can be an antisense molecule (e.g., an antagomiR) complementary to the one or more of: miR- 142-5p, miR-142-3p and miR-374. The agent that increases activity or expression of one or more of: miR-142-5p, miR-142-3p and miR-374 can be a nucleic acid encoding a precursor miR selected from the group consisting of: a precursor form of miR-142-5p, a precursor form of miR-142-3p and a precursor form of miR-374. The nucleic acid can be within a viral vector or a lipid. The cardiovascular disease or disorder can be one of: myocardial ischemia, cardiac failure, familial dilated cardiomyopathy, coronary artery disease, cardiac transplant rejection, hypertensive heart disease, valvular heart disease, viral myocarditis, end-stage cardiomyopathy, arrhythmogenic right ventricular dysplasia, and myocardial scarring due to infarction or other injury. Unless otherwise defined, all technical terms used herein have the same meaning as commonly understood by one of ordinary skill in the art to which this invention belongs.

Additionally described herein is a composition for treating an inflammatory or immunological disorder in a subject. The composition includes a pharmaceutically acceptable carrier and an agent that increases or decreases activity or expression of at least one of: miR-142-5p and miR-142-3p, in an amount effective for alleviating or treating the inflammatory or immunological disorder in the subject. The agent that increases or decreases activity or expression of one or more of: miR-142-5p and miR-142-3p can be an antisense molecule (e.g., an antagomiR) complementary to the one or more of: miR-142-5p and miR-142-3p. The agent that increases activity or expression of one or more of: miR-142-5p, miR-142-3p and miR-374 can be a nucleic acid encoding a precursor miR such as: a precursor form of miR-142-5p, a precursor form of miR-142-3p and a precursor form of miR-374. The nucleic acid can be within a viral vector or a lipid. The inflammatory or immunological disorder can be one of: inflammatory bowel disease, lupus erythematosus, sclerodema, rheumatoid arthritis, organ transplant rejection, Sjogren's syndrome, psoriasis, septic shock, transfusion reaction, anaphylaxis, urticaria, food or drug allergic reaction, dermatomyositis, vasculitis, type I diabetes, multiple sclerosis, immune complex glomerulonephritis, adult respiratory distress syndrome, autoimmune thyroiditis, Goodpasture's syndrome, and any condition in which autoantibodies are produced. The inflammatory or immunological disorder can be one that results from excessive or harmful activation of the immune system, allergic reaction, graft vs. host disease, or organ transplant rejection.

Still further described herein is a cell (e.g., a plurality of cells) for ex vivo therapy that has been transduced with at least one nucleic acid sequence encoding one of: miR-20a, miR-142-5, miR-142-3p, miR-374, antisense sequence complementary to miR-20a, antisense sequence complementary to miR-142-5, antisense sequence complementary to miR-142-3p, and antisense sequence complementary to miR-374. The cells have at least one of: increased potential to differentiate into vascular tissue, and increased survival, compared to the same cell that was not transduced with the at least one nucleic acid sequence. The cell can be one or more of: bone marrow-derived cells, heart cells, and hematopoietic progenitor cells derived from host tissue or from immunocompatible donors.

The cell has increased angiogenic and survival capacity function compared to the same cells that were not transduced with the at least one nucleic acid sequence.

Yet further described herein is a method of treating a cardiovascular disease or disorder in a subject. The method includes administering to the subject a composition including a pharmaceutically acceptable carrier and an agent that decreases expression or activity of miR-20a in an amount sufficient for increasing cardiac or other tissue angiogenesis in the subject. The cardiovascular disease or disorder can be one of: myocardial ischemia, cardiac failure, coronary artery disease, peripheral limb ischemia, cerebrovascular disease, thromboangiitis obliterans, diabetic vasculopathy, microvascular insufficiency, peripheral arterial obstructive disease, and carotid artery atherosclerosis.

Also described herein is a method of treating a cardiovascular disease or disorder in a subject. The method includes administering to the subject a composition including: a pharmaceutically acceptable carrier and an agent that downregulates activity or expression of one or more of: miR-142-5p, miR-142-3p and miR-374, in an amount sufficient to promote cardiac cell survival and enhance cardiac function in the subject. The cardiovascular disease or disorder can be one of: hypertensive cardiomyopathy, heart failure, ischemic heart disease, dilated cardiomyopathy, hypertrophic cardiomyopathy, coronary artery disease, myocardial infarction, and myocardial ischemia-reperfusion damage, and the agent that downregulates activity or expression of one or more of: miR-142-5p, miR-142-3p and miR-374 can be an antisense molecule having complementarity to the precursor or mature sequence of one or more of miR-142-5p, miR-142-3p and miR-374.

Still further described herein is a method for treating an inflammatory or immunological disorder in a subject. The method includes administering to the subject a composition including a pharmaceutically acceptable carrier and an agent that increases or decreases activity or expression of at least one of: miR-142-5p and/or miR-142-3p, in an amount effective for alleviating or treating the inflammatory or immunological disorder in the subject. The inflammatory or immunological disorder can be one of: inflammatory bowel disease, lupus erythematosus, sclerodema, rheumatoid arthritis, organ transplant rejection, Sjogren's syndrome, psoriasis, septic shock, transfusion reaction, anaphylaxis, urticaria, food or drug allergic reaction, dermatomyositis, vasculitis, type I diabetes, multiple sclerosis, autoimmune hepatitis, immune complex glomerulonephritis, adult respiratory distress syndrome, autoimmune thyroiditis, Goodpasture's syndrome, and any condition in which autoantibodies are produced. In one embodiment, the inflammatory or immunological disorder is autoimmune hepatitis and the agent that increases activity or expression of at least one of: miR-142-5p and miR-142-3p is an antisense molecule having complementarity to a precursor or mature sequence of the at least one of: miR-142-5p and miR-142-3p, or a vector encoding the antisense molecule.

Also described herein is a method of inducing differentiation of a plurality of stem or progenitor cells into a cell type such as: endothelial cells, smooth muscle cells, and cardiac myocytes. The method includes transducing the plurality of stem or progenitor cells with at least one nucleic acid of: miR-20a, miR-142-5, miR-142-3p, and miR-374, under culture conditions that result in the differentiation of the plurality of stem or progenitor cells into a cell type such as endothelial cells, smooth muscle cells, and cardiac myocytes. In one embodiment, the differentiated plurality of cells are for ex vivo transplantation, and the method further includes harvesting the differentiated plurality of cells in a suitable medium for transplantation.

Additionally described herein is an ex vivo method of treating heart failure or cardiac vascular disease in a subject. The method includes the steps of: obtaining at least one of: bone marrow progenitor cells, cardiac tissue progenitor cells, epithelial progenitor cells, and circulating progenitor or hematopoietic cells from the subject; transducing the cells with at least one antisense molecule having complementarity to a precursor or mature sequence of one or more of microRNA 142-5p and 142-3p, or a vector encoding the at least one antisense molecule under conditions that result in reduced expression of at least one of: miR-142-3p and miR-142-5p; and administering the transduced cells to the subject in an amount effective for improving cardiac function and alleviating heart failure or cardiac vascular disease in the subject. The transduced cells have improved survival, engraftment capacity and function compared to the same cells that were not transduced with the at least one nucleic acid sequence.

Further described herein is an ex vivo method of preventing or treating organ or tissue transplant rejection in a subject. The method includes the steps of: delivering a composition including a pharmaceutically acceptable carrier and an agent that increases or decreases expression or activity of miR-142-5p, or miR-142-3p in an amount sufficient for suppressing an immune response to the organ or tissue to be transplanted prior to transplantation of the organ or tissue into the subject.

Yet further described herein is a kit for treating a cardiovascular or immunological disease in a subject. The kit includes: any of the compositions or cells described herein, packaging; and instructions for use. In another embodiment, a kit for diagnosing a cardiovascular or immunological disease in a subject includes at least one reagent for detecting plasma, serum or tissue levels of at least one of: miR-20a, miR-142-5p, miR-142-3p, and miR-374; at least one control; packaging; and instructions for use.

As used herein, a "nucleic acid" or a "nucleic acid molecule" means a chain of two or more nucleotides such as RNA (ribonucleic acid) and DNA (deoxyribonucleic acid), and chemically-modified nucleotides. A "purified" nucleic acid molecule is one that is substantially separated from other nucleic acid sequences in a cell or organism in which the nucleic acid naturally occurs (e.g., 30, 40, 50, 60, 70, 80, 90, 95, 96, 97, 98, 99, 100% free of contaminants). The terms include, e.g., a recombinant nucleic acid molecule incorporated into a vector, a plasmid, a virus, or a genome of a prokaryote or eukaryote. Examples of purified nucleic acids include cDNAs, micro-RNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

By the term "gene" is meant a nucleic acid molecule that codes for a particular protein, or in certain cases, a functional or structural RNA molecule.

By the terms "microRNA," "miRNA" and "miR" are meant a non-coding double-stranded RNA (typically 21 nucleotides in length) and all of its precursor forms as transcribed from genomic DNA (eg pri-miRs) before and after the several processing steps by cellular enzymes generating the final 21 bp form. MicroRNAs may be synthetic or naturally occurring.

As used herein, the term "antagomiR" encompasses any single stranded, double stranded, partially double stranded and hairpin structured chemically modified oligonucleotides that target a microRNA through base complementarity.

When referring to an amino acid residue in a peptide, oligopeptide or protein, the terms "amino acid residue", "amino acid" and "residue" are used interchangeably and, as used herein, mean an amino acid or amino acid mimetic joined covalently to at least one other amino acid or amino acid mimetic through an amide bond or amide bond mimetic.

As used herein, "protein" and "polypeptide" are used synonymously to mean any peptide-linked chain of amino acids, regardless of length or post-translational modification, e.g., glycosylation or phosphorylation.

When referring to a nucleic acid molecule or polypeptide, the term "native" refers to a naturally-occurring (e.g., a wild-type (WT)) nucleic acid or polypeptide.

As used herein, the phrase "sequence identity" means the percentage of identical subunits at corresponding positions in two sequences (e.g., nucleic acid sequences, amino acid sequences) when the two sequences are aligned to maximize subunit matching, i.e., taking into account gaps and insertions. Sequence identity can be measured using sequence analysis software (e.g., Sequence Analysis Software Package from Accelrys CGC, San Diego, Calif.).

The phrases "isolated" or biologically pure" refer to material (e.g., nucleic acids, viruses, proteins, peptides, cells, etc.) which is substantially or essentially free from components which normally accompany it as found in its native state.

The term "labeled," with regard to a nucleic acid, protein, probe or antibody, is intended to encompass direct labeling of the nucleic acid, protein, probe or antibody by coupling (i.e., physically or chemically linking) a detectable substance (detectable agent) to the nucleic acid, protein, probe or antibody.

By the term "progenitor cell" is meant any somatic cell which has the capacity to generate functional progeny by proliferation and differentiation. In another embodiment, progenitor cells include progenitors from any tissue or organ system, including, but not limited to, blood, nerve, muscle, skin, gut, bone, kidney, liver, pancreas, thymus, and the like. Progenitor cells are distinguished from "differentiated cells," which are defined in another embodiment, as those cells which may or may not have the capacity to proliferate, i.e., self-replicate, but which are unable to undergo further differentiation to a different cell type under normal physiological conditions. In one embodiment, progenitor cells are further distinguished from abnormal cells such as cancer cells, especially leukemia cells, which proliferate (self-replicate) but which generally do not further differentiate, despite appearing to be immature or undifferentiated.

As used herein, the term "totipotent" means an uncommitted progenitor cell such as embryonic stem cell, i.e., both necessary and sufficient for generating all types of mature cells. Progenitor cells which retain a capacity to generate a more limited number of differentiated cell lineages are termed "pluripotent."

As used herein, the phrases "bone marrow-derived progenitor cells" and "BM-derived progenitor cells" mean progenitor cells that come from a bone marrow stem cell lineage. Examples of bone marrow-derived progenitor cells include bone marrow-derived mesenchymal stem cells (MSC) and EPCs.

By the phrases "therapeutically effective amount" and "effective dosage" is meant an amount sufficient to produce a therapeutically (e.g., clinically) desirable result; the exact nature of the result will vary depending on the nature of the disorder being treated. The compositions described herein can be administered from one or more times per day to one or more times per week. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions and cells described herein can include a single treatment or a series of treatments.

As used herein, the term "treatment" is defined as the application or administration of a therapeutic agent (e.g., cells, a composition) described herein, or identified by a method described herein, to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

The terms "patient" "subject" and "individual" are used interchangeably herein, and mean a mammalian subject to be treated, with human patients being preferred. In some cases, the methods described herein find use in experimental animals, in veterinary applications, and in the development of animal models for disease, including, but not limited to, vertebrates, rodents including mice, rats, and hamsters, as well as non-human primates.

Although compositions, cells, kits and methods similar or equivalent to those described herein can be used in the practice or testing of the present invention, suitable compositions, cells, kits and methods are described below. All publications, patent applications, and patents mentioned herein are incorporated by reference in their entirety. In the case of conflict, the present specification, including definitions, will control. The particular embodiments discussed below are illustrative only and not intended to be limiting.

DETAILED DESCRIPTION

Figure 1:
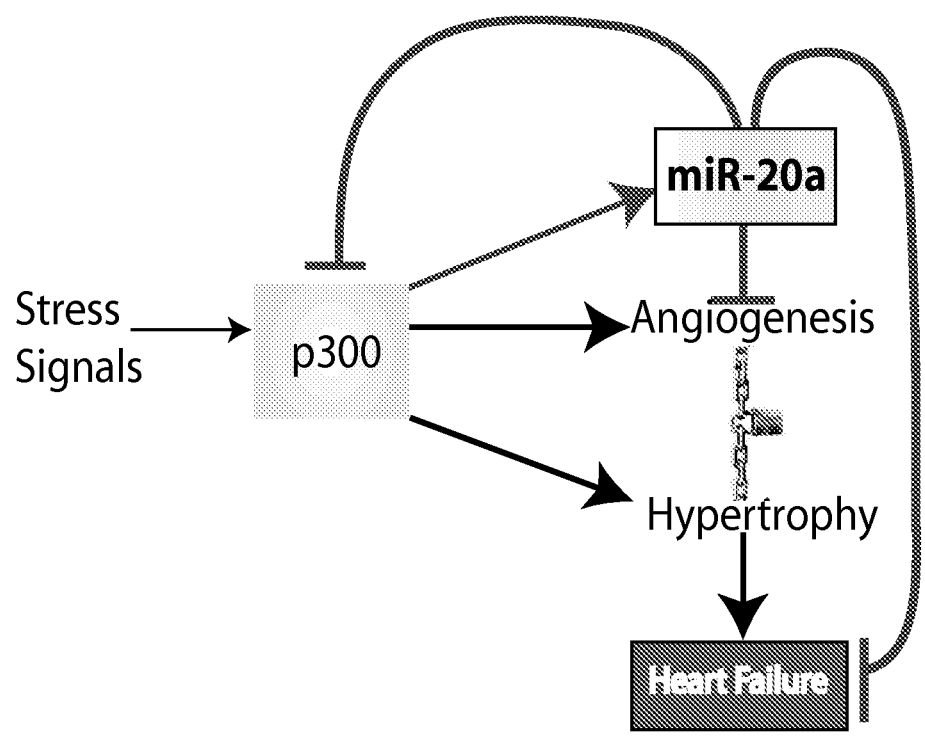
FIG. 1 is a model of the miR20-p300 feedback loop during hypertrophy. Stress signals acting on the myocardium induce p300 expression, which results in the activation of angiogenic and hypertrophic transcriptional programs leading to cardiac hypertrophy. p300 also induces miR-20a, which provides feedback inhibition of p300, reversing both the angiogenic and hypertrophic programs and acting to preserve cardiac function. All aspects of this loop are under temporal regulation.

The compositions, cells, methods and kits described herein can be used to treat a host of diseases including inflammation, cancer, and heart disease (e.g., cardiovascular disease, atherosclerosis, and heart failure. In the experiments described below, the first ever evidence that the microRNAs described herein are novel and unanticipated regulators of the cardiac stress response, and hence therapeutics targeting or manipulating these miR sequences could be useful for the treatment of a number of heart diseases, including myocardial ischemia and heart failure is presented. Many of these micro-RNAs target angiogenesis-associated and inflammatory-associated genes and genes responsible for cardiac cell survival, proliferation and self-renewal. Described herein is the use of miroRNAs identified to be up or down regulated in diseases states such as cardiac failure and myocardial ischemia and antagomirs of these micro-RNAs, as well as the use of cells transduced with these nucleic acids in the treatment of cardiac, immunological, and inflammatory diseases.

The below described preferred embodiments illustrate adaptations of these compositions, cells, kits and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N. Y., 2001; and Current Protocols in Molecular Biology, ed. Ausubel et al., Greene Publishing and Wiley-Interscience, New York, 1992 (with periodic updates). Conventional methods of gene transfer and gene therapy may also be adapted for use in the present invention. See, e.g., Gene Therapy: Principles and Applications, ed. T. Blackenstein, Springer Verlag, 1999; and Gene Therapy Protocols (Methods in Molecular Medicine), ed. P. D. Robbins, Humana Press, 1997. Methods for culturing stem cells, progenitor cells and hematopoietic cells and for autologous progenitor/stem cell therapy are well known to those skilled in the art. See, e.g., Progenitor Cell Therapy for Neurological Injury (Stem Cell Biology and Regenerative Medicine), Charles S. Cox, ed., Humana Press, 1st ed., 2010; A Manual for Primary Human Cell Culture (Manuals in Biomedical Research), Jan-Thorsten Schantz and Kee Woei Ng, World Scientific Publishing Co., 2nd ed., 2010; and U.S. Pat. Nos. 7,790,458, 7,655,225, and 7,799,528. Design and use of antagomirs are described in, for example, U.S. patent application Ser. Nos. 12/787,552 and 12/714,863.

Compositions for Treating Cardiac, Inflammatory and Immunological Diseases

Compositions for treating cardiac, inflammatory and immunological diseases in a subject are described herein. The compositions described herein can be used for treating any type of cardiac-related, inflammation-related, or immunological-related disease or disorder, such as ischemic heart disease, ischemic limb disease, organ transplant rejection, heart failure, inflammatory bowel disease. In a typical embodiment, the compositions include a pharmaceutically acceptable carrier and at least one nucleic acid sequence (e.g., one, two, three, four, etc.) encoding at least one or more miRs (e.g., miR-20a, miR-142-5p, miR-142-3p, miR-374, oligonucleotides containing the seed sequence of these miRs and intended to target the same mRNA transcripts), or at least one antagomir to one or more (e.g., one, two, three, four, five, etc.) miRs (e.g., miR-20a, miR-142-5p, miR-142-3p, miR-374). For example, a composition for treating myocardial ischemia in a subject will typically include anti-miR-20a in an amount effective for improving blood vessel growth and perfusion. As another example, a composition for treating an inflammatory disease such as organ transplant rejection will typically include miR-142-3p and miR-142-5p in an amount effective for reducing the production of inflammatory cytokines by macrophages and other cells in the tissue. As a further example, a composition for treating an immunological disease such as inflammatory bowel disease will typically include miR-142-3p and miR-142-5p in an amount effective for reducing the activity and number of Toll-like receptors.

Methods for synthesizing antagomirs are well known and are described herein. Synthesis of oligonucleotides of a specified length and sequence is a well-established method. Antagomir oligonucleotides used in the compositions, methods, and kits described herein may be additionally stabilized against degradation by chemical modification.

In one embodiment, a composition for treating a cardiac, inflammatory or immunological disease in a subject includes cardiac or bone-marrow-derived autologous progenitor cells transfected or transduced with at least one nucleic acid (e.g., one, two, three, four, etc.) encoding one or more miRs (e.g., miR-20a, miR-142-5p, miR-142-3p, miR-374), or at least one antagomir to one or more (e.g., one, two, three, four, five, etc.) miRs (e.g., miR-20a, miR-142-5p, miR-142-3p, miR-374).

In some embodiments, the compositions include autologous cells infected with a recombinant virus containing at least one nucleic acid (e.g., one, two, three, four, etc.) encoding one or more miRs (e.g., miR-20a, miR-142-5p, miR-142-3p, miR-374), or at least one antagomir to one or more (e.g., one, two, three, four, five, etc.) miRs (e.g., miR-20a, miR-142-5p, miR-142-3p, miR-374). For ex vivo therapy, the progenitor cells are typically isolated from a subject to be treated and have increased angiogenic functions or capabilities compared to the same cells isolated from the subject that were not transduced with the at least one nucleic acid (or infected with a recombinant virus containing the at least one nucleic acid). Any cell type (e.g., differentiated, undifferentiated) can be transfected with DNA sequences. The miRs described herein may be used as biomarkers for cardiovascular and inflammatory disease diagnosis.

Adult stem/progenitor cells may be obtained directly from the bone marrow (for example, from posterior iliac crests), any other tissue, or from peripheral blood. Isolated stem cells and progenitor cells can be maintained and propagated in a cell culture growth medium. Standardized procedures for the isolation, enrichment and storage of stem/progenitor cells are well known in the art. Methods for culturing stem cells, progenitor cells, and hematopoietic cells are well known to those skilled in the art.

The cells which are employed may be fresh, frozen, or have been subject to prior culture. They may be fetal, neonate, adult. Hematopoietic cells may be obtained from fetal liver, bone marrow, blood, cord blood or any other conventional source. The progenitor and/or stem cells can be separated from other cells of the hematopoietic or other lineage by any suitable method.

Marrow samples may be taken from patients with cardiac, immunological, or inflammatory disease (e.g., chronic myocardial ischemia) and enriched populations of hematopoietic stem and/or progenitor cells isolated by any suitable means (e.g., density centrifugation, counterflow centrifugal elutriation, monoclonal antibody labeling and fluorescence activated cell sorting). The stem and/or progenitor cells in this cell population can then be transfected with at least one nucleic acid (e.g., one, two, three, four, etc.) encoding a miR (e.g., miR-20a, miR-142-5p, miR-142-3p, miR-374) or an antagomir(s) to one or more (e.g., one, two, three, four, five, etc.) miRs (e.g., miR-20a, miR-142-5p, miR-142-3p, miR-374) in vitro or ex vivo and can serve as an autologous cellular therapy for cardiac, immunological, or inflammatory disease (e.g., diseases such as ischemic heart failure, organ transplant rejection or peripheral limb ischemia).

Methods of Treating Cardiac, Inflammatory and Immunological Diseases

Methods of treating cardiac, inflammatory and immunological diseases in a subject are described herein. The compositions described herein can be used for treating any type of cardiac-related, inflammation-related, or immunological-related disease or disorder. In one embodiment, a method of treating a cardiovascular disease or disorder (e.g., myocardial ischemia, cardiac failure) in a subject includes administering to the subject a composition that includes a pharmaceutically acceptable carrier and an agent that decreases expression or activity of miR-20a in an amount sufficient for increasing cardiac tissue angiogenesis in the subject. Increasing activity or expression of miR-20a may be useful in reducing the activity of p300, which is deleterious to heart function if levels are too high. Thus miR-20a could be used to improve heart function in hypertensive or valvular cardiomyopathy. In another embodiment, a method of treating a cardiovascular disease or disorder in a subject includes administering to the subject a composition that includes: a pharmaceutically acceptable carrier and an agent that modulates activity or expression of one or more of: miR-142-5p, miR-142-3p and miR-374, in an amount sufficient to promote cardiac cell survival and enhance cardiac function in the subject. For example, by reducing expression of miR-142-5p and/or miR-142-3p, the survival and function of cardiac myocytes is enhanced and overall cardiac function can be improved in various types of heart failure.

In a method for treating an inflammatory or immunological disorder in a subject, a composition including a pharmaceutically acceptable carrier and an agent that increases activity or expression of at least one of: miR-142-5p and/or miR-142-3p, is administered to the subject in an amount effective for alleviating or treating the inflammatory or immunological disorder in the subject. Examples of inflammatory and immunological disorders include organ transplant rejection, psoriasis, lupus erythematosus, and Crohn's disease. For example, by increasing the expression of miR-142-5p or -3p, the production of inflammatory cytokines produced by tissue macrophages and other cells will be reduced, and the production of nitric oxide will also be reduced, diminishing the inflammatory response and minimizing tissue damage.

Methods of Progenitor/Stem Cell Therapy

Methods of progenitor/stem cell therapy are described herein. Such therapy may be autologous progenitor/stem cell therapy or allogenic progenitor/stem cell therapy. These methods result in one or more of: inducing blood vessel growth in the myocardium (i.e., promoting angiogenesis), preventing progression to heart failure, improving cell survival, increasing the numbers of viable myocytes and endothelial cells, and improving the function of existing myocytes. Examples of such therapeutic methods include methods of treating cardiac, immunological, or inflammatory disease in a subject. One embodiment of a method of treating a cardiac, immunological, or inflammatory disease in a subject includes providing and administering a therapeutically effective amount of a composition including bone marrow-derived mesenchymal cells transfected with at least one nucleic acid (e.g., one, two, three, four, etc.) encoding a miR (e.g., miR-20a, miR-142-5p, miR-142-3p, miR-374) or an antagomir(s) to one or more (e.g., one, two, three, four, five, etc.) miRs (e.g., miR-20a, miR-142-5p, miR-142-3p, miR-374). In another embodiment of a method of treating a cardiac, immunological, or inflammatory disease in a subject, a therapeutically effective amount of a composition including progenitor cells infected with a recombinant virus containing at least one nucleic acid (e.g., one, two, three, four, etc.) encoding a miR (e.g., miR-20a, miR-142-5p, miR-142-3p, miR-374) or an antagomir(s) to one or more (e.g., one, two, three, four, five, etc.) miRs (e.g., miR-20a, miR-142-5p, miR-142-3p, miR-374) is administered to the subject in need thereof. The progenitor cells are typically isolated from the subject and have increased survival and capacity to differentiate into functionally relevant cells for the target tissue compared to untransfected progenitor cells isolated from the subject that were not transfected with the at least one nucleic acid or infected with the recombinant virus containing the at least one nucleic acid. In one embodiment, the composition is administered to the subject under conditions and in an effective amount such that regeneration of cardiac tissue is increased in a subject (e.g., increased angiogenesis, increased survival of cardiac myocytes and improved cardiac function) suffering from a cardiac disease such as heart failure or cardiomyopathy. In some methods, a plurality of bone marrow-derived progenitor cells or stem cells are administered to the subject in an amount effective to promote regeneration of cardiac tissue, including cardiac vasculature, in one or more areas of cardiac injury in the subject. In such an embodiment, the bone marrow-derived progenitor cells or stem cells have been transfected with at least one (e.g., one, two, three) nucleic acid (e.g., one, two, three, four, etc.) encoding a miR (e.g., miR-20a, miR-142-5p, miR-142-3p, miR-374) or an antagomir(s) to one or more (e.g., one, two, three, four, five, etc.) miRs (e.g., miR-20a, miR-142-5p, miR-142-3p, miR-374), or infected with a recombinant virus containing at least one (e.g., one, two, three) nucleic acid (e.g., one, two, three, four, etc.) encoding a miR (e.g., miR-20a, miR-142-5p, miR-142-3p, miR-374) or an antagomir(s) to one or more (e.g., one, two, three, four, five, etc.) miRs (e.g., miR-20a, miR-142-5p, miR-142-3p, miR-374). In another embodiment, such a composition is administered to the subject under conditions and in an effective amount such that the local production of nitric oxide and/or inflammatory cytokines is reduced in a subject suffering from an inflammatory disease such as Crohn's disease. As another example, when treating a subject suffering from an immunological disease such as lupus erythematosis, such a composition is administered to the subject under conditions and in an effective amount such that the autoimmune response is blunted.

In these methods, the at least one nucleic acid can be introduced into progenitor or other suitable autologous cells by any suitable method or route. In a typical embodiment, the microRNA or antagomir is delivered to the targeted progenitor or stem cells by introduction of an exogenous nucleic acid expression vector into the cells. Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. The at least one nucleic acid can be included within a virus (sometimes referred to as a "viral vector"), for example. Various techniques using viruses/viral vectors for the introduction of nucleic acids (e.g., antagomirs, miRs) into cells are provided for according to the compositions and methods described herein. Viruses are naturally evolved vehicles which efficiently deliver their genes into host cells and therefore are desirable vector systems for the delivery of therapeutic nucleic acids. Preferred viral vectors exhibit low toxicity to the host cell and produce/deliver therapeutic quantities of the nucleic acid of interest (in some embodiments, in a tissue-specific manner). Retrovirus based vectors have been shown to be particularly useful when the target cells are hematopoietic stem cells. For example, see Baum et al. (1996) J Hematother 5(4):323-9; Schwarzenberger et al. (1996) Blood 87:472-478; Nolta et al. (1996) P.N.A.S. 93:2414-2419; and Maze et al. (1996) P.N.A.S. 93:206-210. Lentivirus vectors have also been described for use with hematopoietic stem cells, for example see Mochizuki et al. (1998) J Virol 72(11): 8873-83. The use of adenovirus based vectors with hematopoietic cells has also been published, see Ogniben and Haas (1998) Recent Results Cancer Res 144:86-92. Viral vector methods and protocols are reviewed in Kay et al. Nature Medicine 7:33-40, 2001. Various techniques known in the art may be used to transfect the target cells, e.g. electroporation, calcium precipitated DNA, fusion, transfection, lipofection and the like.

Also in these methods, the composition or cells can be administered to a subject by any suitable route, e.g., intravenously, or directly to a target site. Several approaches may be used for the introduction of compositions or cells into the subject, including catheter-mediated delivery I.V. (e.g., endovascular catheter), or direct injection into a target site. Techniques for the isolation of autologous stem cells or progenitor cells and transplantation of such isolated cells are known in the art. Ex vivo delivery of cells transduced with recombinant viruses expressing antagomirs or miRs is encompassed by the methods described herein. Ex vivo gene delivery is used to transplant, for example, host cells (e.g., circulating or bone marrow-derived cells that have been transfected with antagomirs or miRs or transduced with recombinant viral vectors (recombinant viruses) encoding antagomirs or miRs back into the host. A suitable ex vivo protocol may include several steps. A segment of target tissue (e.g., BM-derived pluripotent progenitor mesenchymal cells) may be harvested from the host and an appropriate vector may be used to transduce an antagomir-encoding or miR-encoding nucleic acid into the subject's (i.e., host's) cells. These genetically modified cells may then be transplanted back into the subject. Several approaches may be used for the reintroduction of cells into the subject, including intravenous injection, intraperitoneal injection, or in situ injection into target tissue. Microencapsulation of cells transduced or infected with recombinant viral vectors modified ex vivo, for example, is another technique that may be used. Autologous as well as allogeneic cell transplantation may be used according to the invention.

Ex vivo methods of preventing or treating organ or tissue transplant rejection in a subject are described herein. A typical method of preventing or treating organ or tissue transplant rejection in a subject includes the steps of transducing autologous bone marrow-derived or other progenitor cells and administering them intravenously. The cells can be administered to the subject at one or more of the following time points: prior to organ or tissue transplantation, during organ or tissue transplantation, and subsequent to organ or tissue transplantation. In some embodiments, microRNAs and antagomir oligonucleotides can be administered systemically.

The therapeutic methods described herein in general include administration of a therapeutically effective amount of the compositions or cells described herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider. The methods and compositions herein may be also used in the treatment of any other disorders in which downregulation or upregulation of microRNAs or inflammatory signaling molecules may be implicated.

In one embodiment, a method of treating cardiac, immunological, or inflammatory disease in a subject includes monitoring treatment progress. Monitoring treatment progress in a subject generally includes determining a measurement of, for example, tissue damage at the site of injury (cardiac injury) or other diagnostic measurement in a subject having a cardiac, immunological, or inflammatory disease, prior to administration of a therapeutic amount of a composition as described herein sufficient to increase, for example, cardiac tissue growth, cardiac angiogenesis, improved survival of cardiac myocyte and other resident cells, improved cardiac function and electrical stability etc. at the site of cardiac injury in the subject. At one or more time points subsequent to the subject having been administered a therapeutic amount of a composition as described herein sufficient to increase myocardial performance or survival at the site of cardiac injury, a second measurement of cardiac function or tissue damage at the site of cardiac injury is determined and compared to the first measurement of cardiac function or tissue damage. The first and subsequent measurements are compared to monitor the course of cardiac, immunological, or inflammatory disease and the efficacy of the therapy.

Methods of Inducing Differentiation of Stem and Progenitor Cells

Based on the experimental results described herein, particular miRs and antagomirs may be used to induce differentiation of progenitor and stem cells. A method of inducing differentiation of a plurality of stem or progenitor cells into a particular cell type, e.g., endothelial cells, smooth muscle cells, and cardiac myocytes, generally includes transducing the plurality of stem or progenitor cells with at least one or more of the following nucleic acids: miR-20a, miR-142-5, miR-142-3p, and miR-374, under culture conditions that result in the differentiation of the plurality of stem or progenitor cells into the desired particular cell type, e.g., endothelial cells, smooth muscle cells, and cardiac myocytes. In a typical embodiment, the differentiated plurality of cells are for ex vivo transplantation in a subject (e.g., human subject), and the method further includes harvesting the differentiated plurality of cells in a suitable medium for transplantation Kits Described herein are kits for treating cardiac, immunological, or inflammatory disease in a mammalian subject. One example of a kit includes a therapeutically effective amount of a composition described herein, which typically includes at least one (e.g., one, two, three) nucleic acid (e.g., one, two, three, four, etc.) encoding a miR (e.g., miR-20a, miR-142-5p, miR-142-3p, miR-374) or an antagomir(s) to one or more (e.g., one, two, three, four, five, etc.) miRs (e.g., miR-20a, miR-142-5p, miR-142-3p, miR-374), or a recombinant virus containing at least one (e.g., one, two, three) nucleic acid (e.g., one, two, three, four, etc.) encoding a miR (e.g., miR-20a, miR-142-5p, miR-142-3p, miR-374) or an antagomir(s) to one or more (e.g., one, two, three, four, five, etc.) miRs (e.g., miR-20a, miR-142-5p, miR-142-3p, miR-374), as well as instructions for administering the composition to the subject and appropriate packaging. Another example of a kit includes a therapeutically effective amount of a composition that includes bone marrow-derived mesenchymal cells or hematopoietic cells transfected or transduced at least one (e.g., one, two, three) nucleic acid (e.g., one, two, three, four, etc.) encoding a miR (e.g., miR-20a, miR-142-5p, miR-142-3p, miR-374) or an antagomir(s) to one or more (e.g., one, two, three, four, five, etc.) miRs (e.g., miR-20a, miR-142-5p, miR-142-3p, miR-374), or infected with a recombinant virus containing at least one (e.g., one, two, three) nucleic acid (e.g., one, two, three, four, etc.) encoding a miR (e.g., miR-20a, miR-142-5p, miR-142-3p, miR-374) or an antagomir(s) to one or more (e.g., one, two, three, four, five, etc.) miRs (e.g., miR-20a, miR-142-5p, miR-142-3p, miR-374), as well as instructions for administering the composition to the subject and appropriate packaging.

In embodiments in which the composition includes cells, the cells can be packaged by any suitable means for transporting and storing cells; such methods are well known in the art. The instructions generally include one or more of: a description of the cells; dosage schedule and administration for treatment of cardiac, immunological, or inflammatory disease (e.g., heart failure, inflammatory bowel disorders, organ transplant rejection, autoimmune disorders, disorders of increased or reduced blood vessel growth, disorders in which increased apoptotic cell death due to immune activation or ischemia contributes to pathophysiology such as type I diabetes, and cardiomyopathy); precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container. Generally, a kit as described herein also includes packaging. In some embodiments, the kit includes a sterile container which contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding cells or medicaments.

Administration of Compositions

The compositions and cells described herein may be administered to mammals (e.g., rodents, humans) in any suitable formulation. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to mammals by any conventional technique. The compositions may be administered directly to a target site by, for example, surgical delivery to an internal or external target site, or by catheter (e.g., endovascular catheter) to a site accessible by a blood vessel. When treating a subject having, for example, cardiac disease, the composition may be administered to the subject intravenously, directly into cardiovascular tissue, or to the surface of cardiovascular tissue. The compositions may be administered in a single bolus, multiple injections, or by continuous infusion (e.g., intravenously, by peritoneal dialysis, pump infusion). For parenteral administration, the compositions are preferably formulated in a sterilized pyrogen-free form.

Effective Doses

The compositions and cells described herein are preferably administered to a mammal (e.g., human) in an effective amount, that is, an amount capable of producing a desirable result in a treated mammal (e.g., treating a cardiovascular, immunological, or inflammatory disease or disorder). Such a therapeutically effective amount can be determined according to standard methods. Toxicity and therapeutic efficacy of the compositions and cells utilized in methods of the invention can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently.

EXAMPLES

The present invention is further illustrated by the following specific examples. The examples are provided for illustration only and should not be construed as limiting the scope of the invention in any way.

Example 1

Feedback Inhibition of p300 by miR-20a Attenuates Hypertrophy-Associated Angiogenesis and Cardiac Dysfunction Compensatory angiogenesis is thought to be important for the maintenance of cardiac function during hypertrophy. The experiments described below were performed to characterize molecular regulators and functions of angiogenesis during the transition to heart failure.

Methods and Results

In mice expressing a myocyte-restricted transgene encoding acetyltransferase p300, a central regulator of hypertrophy, it was observed that p300 initially drives robust compensatory angiogenic gene expression and blood vessel growth. However, after 5 months, angiogenic transcription fell steeply, together with deteriorating cardiac function and increased expression of miR-20a, a member of the antiproliferative and anti-angiogenic miR-17~92 cluster. In myocardium, p300 bound to a novel enhancer upstream of miR-20a, and adenoviral transduction of p300 specifically upregulated miR-17 and miR-20a in cardiomyocytes. In turn, miR-20a suppressed expression of p300 via sequences in its 3' untranslated region (UTR), reduced expression of downstream genes including sarcomericactin, alpha-actinin, hypoxia inducible factor 1 alpha (HIF-1A), vascular endothelial growth factor A (VEGFA) and multiple other angiogenic transcripts. Lentiviral transduction of miR-20a reduced cardiac progenitor cell (CPC) proliferation and tube formation in Matrigel, and delayed reperfusion in a hind limb ischemia model in vivo, confirming that it is functionally anti-angiogenic. Transduction of miR20a in p300tg mice reduced myocardial expression of p300 and its angiogenic gene targets, associated with durable improvement in cardiac function.

Conclusion: These data identify p300 as a novel target for miR-20a, and show that p300 upregulates miR-20a as part of a negative feedback loop that delays heart failure and represses angiogenic signaling as a secondary effect.

In the normal heart, myocardial mass, vascular density and workload are closely balanced. Numerous studies have shown that this balance is perturbed in many experimental models of cardiac hypertrophy, and in clinical hypertension and aortic stenosis. In pressure-overload hypertrophy, capillary density fails to increase in proportion to cardiac mass, with resulting compromise in delivery of oxygen and nutrients. Hypertrophy appears to be associated with a specific defect in compensatory angiogenesis despite the presence of tissue hypoxia and this deficit has been directly implicated in the conversion of compensatory to pathological hypertrophy in animal models, associated with impaired expression of angiogenic factors such as HIF1a, HIF2a and VEGFR2. However, the mechanisms regulating the attenuated angiogenic response during hypertrophy remain completely understood. It also remains unknown whether interventions to increase angiogenesis would attenuate dysfunction of the hypertrophic myocardium, and thereby delay or reduce the onset of heart failure.

The nuclear histone acetyltransferase (HAT) p300 is a nodal, dose-dependent regulator of the hypertrophic response to pressure overload. A model of myocardial p300 transgenic gain was used as a useful tool for assessing molecular effectors of the pathological transition from hypertrophy to heart failure and for evaluating p300 effectors as targets for therapy. Here it is shown that p300-driven adaptive hypertrophy is accompanied by a marked compensatory angiogenesis through induction of an angiogenic gene program. This initial compensatory phase is followed by a transition to heart failure between 5-8 months in which the same angiogenic genes are strongly suppressed. It was shown that members of the anti-angiogenic miR17~92 cluster are upregulated by p300 during hypertrophy, and that one member, miR-20a, is capable of suppressing the angiogenic transcription program as well as p300 itself, both in vitro and in vivo. Remarkably, in vivo transduction of p300tg hearts with miR-20a is associated with significantly improved cardiac function. It is concluded that titration of p300 by miR-20a serves in an adaptive feedback loop to delay or mitigate cardiac dysfunction, despite concomitant loss of p300-dependent angiogenic signalling.

Experimental Procedures

Materials and Reagents: Mice bearing α-MHC-MEK1 (Sanna et al., Mol Cell Biol 2005; 25:865-78) or α-MHC-calcineurinA (Molkentin et al., Cell 1998; 93:215-228) transgenes and mice expressing α-MHC-driven transgenes encoding either wild type cardiac TnT or the HCM-associated mutant TnT I79N (Miller et al., J Biol Chem 2001; 276:3743-55) were used. Adenovirus vectors encoding p300 or a blank pcDNA3.1 vector were purchased from Cell Biolabs (San Diego, Calif.). Antibodies against p300, HDAC9, IgG and GAPDH were from Santa Cruz City, (Santa Cruz, Calif.); anti-sarcomeric myosin heavy chain (MF20) was from the Hybridoma Bank (Iowa City, Iowa), anti-Vegfa from Abcam (Cambridge, Mass.); and anti-Hif1a from Millipore (Billerica, Mass.). The Amersham ECL Western detection system was obtained from GE Healthcare Bio-Sciences (Piscataway, N.J.). The MirVana PARIS kit (Applied Biosystems/Ambion, Austin, Tex.) was used for microRNA extraction. Reagents for realtime quantitative PCR were obtained from Applied Biosystems, Foster City, Calif., including TaqMan 5' nuclease, Universal PCR Master Mix, MultiScribe reverse transcriptase and transcript-specific probes. Luciferase vectors encoding p300 and control 3'UTR sequences were obtained from Genecopoeia, Rockville, Md.

Mouse surgical models: All animals were treated in accordance with the Guide for the Care and Use of Laboratory Animals (National Institutes of Health), and according to protocols approved by the University of Miami Animal Care and Use Committee. In vivo pressure overload was created in wild type and genetically modified mice by creation of a surgical restriction in the transverse aorta between the origins of the right and left carotid arteries as described previously (Wei et al., Circulation 2008; 118:934-46). Myocardial infarction was modeled as previously described (Gerhmann et al., Basic Res Cardiol 2001; 96:237-50), with minor modifications. Hindlimb ischemia was created in mice using a variation of a previously published method (Hazarika et al., Circ Res 2007; 101:948-56).

In vivo transduction of miR-20a: Newborn (5 day) p300tg pups (BS line) received 8×108 viral particles of miR-20a or a scrambled sequence (ct-miR) via external jugular vein injection.

Microscopy and Stereology: Wild type and p300tg (BS line) littermates were anesthetized and sacrificed by cervical dislocation. Total heart weight and left ventricle, liver and kidney weight and right tibia length were determined. Tissues were fixed in 4% paraformaldehyde in PBS and embedded in paraffin for histology and immunofluorescence imaging using standard methods. Stereological analysis was performed as previously described (Wei et al., Circulation 2008; 118:934-46).

Western Blots: Immunoblotting was performed using standard methods.

Microarray analysis: RNA was prepared from left ventricles of wild type and p300tg littermate mice (BS line) at defined ages, and hybridized on Affymetrix Mouse Genome 430 2.0 GeneChip expression arrays (45,101 probe sets) following the manufacturer's protocols. Data were analyzed using the GeneSpringsoftware suite (Silicon Genetics, Redwood City, Calif.).

Adenoviral transduction of p300 in Primary Cardiac Myocytes: Cardiac myocytes were isolated from d1-3 neonatal Sprague-Dawley rat pups and plated in 60 mm culture dishes in MEM+5% FBS. On the next day, cells were transduced using adenovirus encoding p300 or a blank pcDNA3.1 vector, and maintained thereafter in a defined serum-free medium. Cells were harvested 48 hours after transduction and RNA was isolated as described above.

CPC Proliferation and Matrigel Assays: CPC were isolated by Sca-1 affinity and cloned by serial dilution from adult mouse ventricular muscle. Untransfected or lentivirus vector-transduced CPCs were plated in 60 mm tissue culture dishes at a density of 5×104 per plate and counted daily for 6 days on a Coulter Counter (Beckman). An in vitro assay of angiogenic potential was carried out as described 12, with modifications.

Luciferase 3'UTR Assay: Luciferase vectors containing either full-length p300 3' UTR or a control 3' sequence were transfected into 293T cells stably overexpressing miR-20a or a scrambled control microRNA using Lipofectamine 2000 (Invitrogen). 48 hours post-transfection, cell extracts were assayed for luciferase activity using the Luc-Pair miRluciferase assay kit (Genecoepia). Relative reporter activities were finally expressed as luminescence units normalized to co-transfected Renilla luciferase activity in the same extracts.

Statistical Analysis: For qRT-PCR mRNA analyses and all other statistical tests, differences between groups were assessed by one-way ANOVA. In all cases, the acceptance level of significance was $p<0.05$ using a two-tailed distribution. All transgenic mouse measurements were made in comparison to wt littermates.

Results p300 induces blood vessel growth in the myocardium: In p300tg mice, myocardial p300 levels were increased to ~2.5× wt, accompanied by a significant increase in absolute and normalized heart weight relative to their wt littermates. In addition, p300tg hearts showed enhanced angiogenesis, with prominentepicardial and intramyocardial coronary arteries and perivascular elastin and collagen indicative of mature vessels. Quantitative stereological analysis confirmed significant increased density and length of intramyocardial blood vessels between 1-3 months of age.

Early induction and late repression of angiogenic transcription in p300-driven hypertrophy: p300tg myocardial gene expression profiles at 1 month of age, shortly after transgene activation, revealed broad induction of angiogenesis-associated genes (≥1.4×, $p<0.02$, Table 1). HIF-1A protein levels were elevated at 3 months (2.6±0.47 fold, $p<0.05$). Selected genes were subsequently confirmed by RT-PCR assay, along with a further 4 genes (Egr3, Egr2, Fgf9, and Vegfc). Of these, 6 (Angpt1, Fgf9, Vegfa, Hif1α, Sox4, and Egln3) were significantly induced in other mouse models of hypertrophy (Table 2), and 3 showed significant co-regulation with p300 (FGF9, $r2=0.83$; Sox4, $r2=0.60$; VEGFA, $r2=0.53$). Chromatin immunoprecipitation assay confirmed p300 binding to these gene promoters. Angiogenic gene expression was further elevated at 5 months; however, by 8 months all transcripts were drastically reduced relative to levels in wt hearts.

p300 induces expression of the miR-17~92 cluster: The 3'UTR regions of several p300-targeted genes, as well as p300 itself, contain a common binding site for 2 members of the miR17~92 cluster, miR-17-5p and 20a, and HIF1a has previously been shown to be a direct target of miR-17~92 (Taguchi et al., Cancer Res 2008; 68:5540-5). All members of the miR-17~92 cluster were expressed in all 4 heart chambers and in all other tissues examined. MiR-17~92 expression trended higher in p300tg hearts in all chambers. Significant upregulation was observed for miR-17-3p, miR-17-5p, miR-20a and miR-92 (2.5-3.0×) in the left atrium and miR-20a (1.9×) in ventricles of 40 day old mice; miR-17-3p was increased 3.0× in the LV at 9 months (p300tg vs. wt, n=3 per group, all $p<0.05$).

When an increase in p300 levels was forced via adenoviral p300 vector transduction of neonatal rat cardiomyocytes, expression of all 3' cluster members was coordinately increased, including miR-20a (2.26-fold±0.03, $p<0.0001$).

Expression of an unrelated miRNA, miR-199, was unchanged. Chromatin immunoprecipitation of left ventricular myocardium identified direct binding of p300 to a region 500 bp upstream of miR-20a that has consensus binding sites for MEF2 and GATA4, and which also bound HDAC-9. No significant binding of p300 was observed in 1 kb regions flanking this enhancer. Binding of p300 was consistently higher in p300tg myocardium than in wt hearts (n=3).

miR-20a represses the angiogenic gene expression program and angiogenesis in CPCs: Angiogenesis in the myocardium is thought to arise in part from the differentiation of resident pluripotent stem/precursor cells. Therefore the effect of miR-20a on the growth and angiogenic differentiation of murine c-kit+ CPCs was determined. Lentiviral overexpression of miR-20a, but not a scrambled sequence (Scherr et al., Nucleic Acids Res 2007; 35:e149), markedly slowed CPC proliferation, with no effect on cell viability. Mir-20a also reduced F-actin staining and sarcomeric organization in both CPCs and cardiac myocytes, and reduced expression of VEGF-A (0.3 fold±0.24, $p<0.05$) and α-actinin (0.58±0.22, $p<0.05$). Increased expression of miR-20a in CPCs was associated with the repression of a broad range of angiogenic genes, including HIF-1 and p300, recapitulating the angiogenic profile of 8-month p300tg hearts; this was associated with direct targeting of the 3'UTR of p300 by miR-20a. The ability of CPCs to form endothelial tube-like structures in Matrigel, a functional assay for angiogenic capacity, was specifically compromised by forced expression of miR-20a above very low to undetectable baseline levels. Further evidence for a functional anti-angiogenic effect of miR-20a in vivo was obtained in a mouse hindlimb ischemia model.

Transduction of miR-20a represses cardiac p300 and prevents progression to heart failure in p300tg hearts: Mice transduced on d1-3 with lentivirus mature miR-20a or a scrambled sequence (ct-miR) were assessed at 3 months of age. Altered levels of miR-20a were not detected in the hearts or livers of these mice by qPCR. However, mice that received miR-20a had significantly reduced myocardial p300 and brain natriuretic peptide (Nppb) expression, and significant reversal of a gene expression signature of myocardial p300 overexpression (Table 3). Mir-20a transduction resulted in improved ejection fraction, fractional shortening, and systolic and diastolic left ventricular dimensions relative to the ct-miR-injected and non-transduced control hearts. While HW/BW and HW/TL were not significantly changed by miR-20a transduction, body weights and normalized liver weights were significantly less in the miR-20a-injected mice relative to the control-injected mice, consistent with the improvement in ventricular hemodynamics.

The experiments described herein show that myocyte p300 drives both hypertrophy and compensatory angiogenesis, while inducing counter-regulatory microRNAs that terminate both signals. Induction of acetyltransferase p300 in the cardiac myocyte induced substantial conduit blood vessel growth in the myocardium, together with activation of a broad angiogenic transcription program that includes targets for p300, including HIF-1 and VEGF. Also, p300 was identified as a novel target for a microRNA, miR-20a, that has been implicated in the negative regulation of angiogenesis through its ability to target VEGF and HIF-1. These data show that miR-20a is directly activated by p300, and subsequently plays a critical role in negative feedback inhibition of the hypertrophic response, including the repression of angiogenic transcription (FIG. 1). Similar negative feedback loops have been described for miR20a, E2F and Myc (31-34).

TABLE 1

Angiogenic genes differentially expressed in 1 month p300tg hearts (microarray).

| Gene Symbol | Gene Name |
|---|---|
| Fgf6 | fibroblast growth factor 6 |
| Myc | myelocytomatosis oncogene |
| Thbs4 | thrombospondin 4 |
| Nppb | natriuretic peptide precursor type B |
| Timp1 | tissue inhibitor of metalloproteinase 1 |
| Fos | FBJ osteosarcoma oncogene |
| Tnfrsf12a | tumor necrosis factor receptor superfamily, member 12a |
| Tgfb2 | transforming growth factor, beta 2 |
| Amot | angiomotin |
| Cyr61 | cysteine rich protein 61 |
| Ctgf | connective tissue growth factor |
| Thbs1 | thrombospondin 1 |
| Col5a2 | procollagen, type V, alpha 2 |
| Bgn | biglycan |
| Ctss | cathepsin S |
| Hbegf | heparin-binding EGF-like growth factor |
| Gna13 | guanine nucleotide binding protein, alpha 13 |
| Bmp4 | bone morphogenetic protein 4 |
| Adamts1 | a disintegrin-like and metallopeptidase |
| Celsr1 | cadherin EGF LAG seven-pass G-type receptor 1 |
| Dpys13 | dihydropyrimidinase-like 3 |
| Dynll1 | dynein light chain LC8-type 1 |
| Fbln2 | fibulin 2 |
| Itga5 | integrin alpha 5 |
| S100a4 | S100 calcium binding protein A4 |
| Notch2 | Notch gene homolog 2 (Drosophila) |
| Rtn4 | reticulon 4 |
| Junb | Jun-B oncogene |
| Cd44 | CD44 antigen |
| Pdgfa | platelet derived growth factor, alpha |
| Crhr2 | corticotropin releasing hormone receptor 2 |

TABLE 2

Co-regulation of p300 and angiogenic genes in 7 genetic and surgical mouse models of hypertrophy.

| p300 | Calcineurin | MEK1 | TNT | TNT Mut | TAC2h | TAC48h | TAC72h | MI24h | MI48h | Gene Symbol |
|---|---|---|---|---|---|---|---|---|---|---|
| 7.4 | 0.9 | 1.2 | 0.9 | 1.0 | 4.4 | 0.5 | 0.9 | 1.3 | 1.4 | Ep300 |
| 1.1 | 0.3 | 0.4 | 0.5 | 0.1 | 1.2 | 1.0 | 0.3 | 0.6 | 0.8 | Angpt1 |
| 1.5 | 0.8 | 0.9 | 0.7 | 0.7 | 1.3 | 0.5 | 1.6 | 2.3 | 1.8 | Egln3 |
| 2.5 | 1.0 | 0.6 | 0.6 | 0.5 | 1.4 | 0.7 | 0.8 | 0.5 | 1.3 | Fgf9 |
| 1.3 | 1.1 | 1.0 | 0.8 | 0.8 | 1.9 | 0.8 | 1.0 | 1.8 | 1.5 | Vegfa |

TABLE 2-continued

Co-regulation of p300 and angiogenic genes in 7 genetic and surgical mouse models of hypertrophy.

| p300 | Calcineurin | MEK1 | TNT | TNT Mut | TAC2h | TAC48h | TAC72h | MI24h | MI48h | Gene Symbol |
|---|---|---|---|---|---|---|---|---|---|---|
| 1.3 | 1.0 | 1.4 | 1.3 | 1.3 | 1.5 | 1.4 | 1.2 | 2.4 | 1.9 | Hif1a |
| 3.5 | 0.4 | 1.0 | 0.9 | 1.0 | 1.1 | 0.8 | 1.4 | 1.0 | 2.2 | Sox4 |

*Selected angiogenic genes were assayed by qPCR in mice following surgical interventions at indicated time points, and in 4 transgenic models of hypertrophy. Fold changes relative to sham-operated or wild-type littermates are shown. TAC = transverse aortic coarctation, 2, 24 and 48 hours, with sham controls. MI = permanent coronary occlusion; p300 = α-MHC-p300 transgene; MEK1 = α-MHC-MEK1 transgene (Sanna et al., Mol Cell Biol 2005; 25:865-78); CnA = α-MHC-calcineurinA transgene (Molkentin et al., Cell 1998; 93: 215-28); TnT = α-MHC-wildtype cardiac TnTtg; TnT I79N = α-MHC-I79N TnTtg (Miller et al., J Biol Chem 2001; 276: 3743-5). For each model, N = 3 females per group. All transgenic mice were analyzed at 1 month of age; surgical models at 3 months (see Methods).

TABLE 3 p300-induced genes repressed by MiR-20a transduction in vivo. A previously defined subset of 86 transcripts specifically upregulated in p300tg vs wt littermate hearts (Dews et al., Nat Genet 38: 1060-1065, 2006) was assessed by qPCR 3 months after transduction with miR-20a or a scrambled sequence. Ratio of expression in miR20a/scrambled miR is shown (fold change). Significantly altered genes are shown, constituting more than a third of the total; almost all were repressed. N = 4-6 mice per group. Presence or absence of a predicted miR-20a binding site in the 3'UTR of the corresponding gene (according to TargetScan) is indicated.

| Gene Symbol | fold change | p-value | SD | Predicted Mir-20a binding site present in 3' UTR |
|---|---|---|---|---|
| Ereg | 0.25 | 0.0004 | 0.06 | Yes |
| Ptprf | 0.60 | 0.0008 | 0.27 | Yes |
| Adam19 | 0.48 | 0.0016 | 0.10 | No |
| Ube2c | 0.22 | 0.0022 | 0.11 | No |
| Egln3 | 0.43 | 0.0032 | 0.08 | Yes |
| Timp1 | 0.38 | 0.0034 | 0.16 | No |
| Popdc3 | 0.50 | 0.0036 | 0.11 | Yes |
| Uck2 | 0.51 | 0.0040 | 0.09 | No |
| Ssbp2 | 0.70 | 0.0059 | 0.16 | Yes |
| Cpxm2 | 0.57 | 0.0077 | 0.13 | No |
| Slc35a5 | 0.66 | 0.0089 | 0.14 | No |
| Trpv2 | 0.59 | 0.0092 | 0.19 | No |
| Igfbp5 | 0.61 | 0.0124 | 0.04 | No |
| Nppb | 0.34 | 0.0165 | 0.20 | No |
| Csdc2 | 0.65 | 0.0175 | 0.17 | No |
| Vegfb | 0.66 | 0.0178 | 0.39 | No |
| Tyrobp | 0.61 | 0.0186 | 0.08 | No |
| Ppp1r3b | 0.62 | 0.0209 | 0.18 | Yes |
| Fgf2 | 0.76 | 0.0210 | 0.16 | No |
| Snd1 | 0.69 | 0.0217 | 0.12 | No |
| Kif3b | 0.68 | 0.0226 | 0.19 | Yes |
| Tgfb2 | 0.59 | 0.0230 | 0.12 | No |
| Dio2 | 0.43 | 0.0266 | 0.58 | No |
| Klf4 | 0.62 | 0.0287 | 0.25 | No |
| Angpt2 | 0.62 | 0.0296 | 0.27 | Yes |
| Fos | 0.53 | 0.0301 | 0.20 | No |
| Nkain1 | 0.57 | 0.0303 | 0.18 | No |
| Lrrc33 | 0.54 | 0.0319 | 0.14 | No |
| Pkig | 0.77 | 0.0401 | 0.14 | No |
| Gdpd1 | 0.66 | 0.0414 | 0.26 | No |
| Amot | 0.62 | 0.0419 | 0.13 | No |
| Fgf9 | 0.73 | 0.0429 | 0.10 | No |
| Gsta2 | 0.21 | 0.0529 | 0.29 | No |
| Lmo2 | 0.69 | 0.0531 | 0.13 | No |

Example 2

Global Inhibition of Myocardial Cytokine Signaling by miR-142 is Reversed During Cardiac Growth Through p300 and MAPK Activation An increase in cardiac workload generates oxidative stress, and therefore requires the activation of both survival and growth signal pathways. In the experiments described below, it was shown that microRNA-142 is universally repressed by cardiac growth signals; when present, it inhibits both survival and growth pathways by directly targeting the nodal regulators acetyltransferase p300 and IL6st. It was also shown that miR142 also potently represses multiple components of the NF-κB pathway, preventing cytokine-mediated NO production, and blocks translation of α-actinin. MiR-142 is repressed in models of hypertrophy in vivo, and in human cardiomyopathic hearts; and is inversely related to p300 and MAPK activity. Forced expression of miR142 during hypertrophic growth induced extensive apoptosis and cardiac dysfunction; conversely, loss of miR-142 fully rescued cardiac function in a heart failure model. It was concluded that downregulation of miR-142 is required to enable myocyte survival during the adaptation to hemodynamic stress.

The data described below show that miR-142-5p and -3p, products of the same primary transcript, are downregulated during cardiac hypertrophy by mechanisms requiring p300 and MAP kinase activity; also shown was that this repression is essential for successful cardiac adaptation to changing hemodynamic demand in vivo. Mechanistically, it was shown that miR-142 directly targets nodal regulators of two critical pathways for cardiac adaptive hypertrophy: p300, a quantitative regulator of growth, and IL6st, which transmits cytokine-mediated survival signals to JAK/STAT; another direct target is α-actinin, an essential component of the cardiac cytoskeleton. Most strikingly, it was demonstrated that miR-142 is a global inhibitor of cytokine signaling and function in the myocardium.

Results miR-142-5p is expressed and dynamically regulated during cardiac growth in vivo. An initial analysis of left ventricular myocardium comparing α-MHC-p300 transgenic mice (Wei, J. Q., et al. Circulation 118, 934-946 (2008)) and their wild type littermates indicated differential regulation of a small set of microRNAs, including miR-142-5p and -3p. In both p300tg and wt mice, miR-142-5p levels were relatively low in the period of adaptive cardiac growth between birth and adulthood at 2 months, rising sharply at 3 months, then returning to baseline by 5 months. At 3 months, miR-142-5p was approximately 10% as abundant as miR-142-3P, which was expressed at levels close to those of the highly abundant species miR-1 and miR-let-7c. Levels of miR-142 were inversely regulated with p300 in various hypertrophy models: miR-142-5p was significantly lower in p300-overexpressing myocardium at all time points, in wt mouse hearts following acute surgically induced pressure overload, and in human hearts with various types of cardiomyopathy, where p300 is also upregulated (Wei, J. Q., et al. Circulation 118, 934-946 (2008)).

miR-142-5p and -3p are downregulated during the onset of cardiac hypertrophy. Next, the kinetics of miR-142 repression by growth signals was examined, using a model of serum-induced cardiac myocyte hypertrophy in culture (Bishopric, N. H. & Kedes, L. Proc. Natl. Acad. Sci. USA 88, 2132-2136 (1991)). 5% fetal calf serum (FCS) induced robust hypertrophy of neonatal rat cardiac myocytes, accompanied by a large rise in p300 levels within 2 hours that persisted for at least 36 hours. Over the same interval, both miR-142-5p and -3p were down-regulated to ~50% of basal levels and remained suppressed for at least 24 hours. Interestingly, the drop in miR-142-3p levels was more rapid and persisted longer than that of miR-142-5p. Suppression was specific to miR-142, as the unrelated microRNA miR17-3p was upregulated under the same conditions.

Growth factor-induced repression of miR-142 is reversed by multiple MAP kinase inhibitors. Serum contains a mixture of growth factors that signal through one or more mitogen-activated protein kinase (MAPK) cascades, culminating in activation of the terminal effectors p38 MAPK, c-jun N-terminal kinases (JNKs) and p42/44 extracellular signal-regulated kinases (ERKs). The downstream phosphorylation of specific intracellular targets results in modulation of cardiac gene expression as a part of the hypertrophic response. To interrogate the role of MAPK signaling in repression of miR-142, cardiac myocytes were stimulated with serum in the presence of well-characterized inhibitors of MEK1 (UO126), p42/p44 MAPK/ERK (PD98059) p38MAPK (SB202190) or c-Jun N-terminal kinase (JNK, SP600125) using concentrations previously shown to be at least partially selective for their respective targets. Treatment with any of these compounds reversed the serum-induced downregulation of miR-142-5p and -3p. In addition, all inhibitors increased basal levels of miR-142-3p. These results indicate that miR-142-5p and 3p are negatively regulated by serum growth factors, acting either through a combination of MAP kinases, or possibly through a single kinase that is inhibited by all 4 compounds.

Repression of miR-142 by p300. Both ERK/MAPK and p38MAPK have been reported to phosphorylate and modulate the activity of p300. To determine whether p300 directly regulates miR-142, cardiac myocytes were transduced with an adenovirus expressing full-length human p300 (Ad-p300), or transfected them with an anti-p300 silencing RNA (siRNA). Ad-p300, but not a blank Ad-GFP virus, significantly increased protein levels of p300 at 48 hours, accompanied by a reduction in both miR-142-5p and -3p. Conversely, cardiac myocytes transfected with anti-p300 siRNA but not with a non-silencing sequence (ns) had >70% reduction in p300 levels at 48 h, and this was accompanied by more than doubling of both miR-142-5p and -3p expression. Thus, p300 is both necessary and sufficient to drive the repression of miR-142 in the absence of hypertrophic extracellular signals or MAPK activation.

MiR-142 directly targets p300. A query using the TargetScan microRNA target prediction algorithm revealed a predicted binding site for miR-142-5p in the p300 3'UTR, suggesting that miR-142 might reciprocally inhibit p300. To investigate this, cardiac myocytes were transfected with lentiviral vectors containing either the hairpin structure encoding both miR-142-5p and -3p (miR-142), or a non-targeting scrambled sequence (NT). Both miRs were expressed from the miR-142 lentivirus, accompanied by a marked decrease in p300 protein levels. A luciferase expression vectors containing the wild type p300 3'UTR was efficiently repressed by miR-142. Mutation of the predicted miR-142-5p binding site eliminated this repression, confirming a direct repression of p300 by miR-142-5p.

MiR-142 targets α-actinin. The majority of genes targeted by microRNAs are thought to be regulated through mRNA transcript destabilization. Other genes may be regulated indirectly (e.g. if their direct regulators are targeted), amplifying the physiological effects of miRNA loss and gain. To get a picture of the functional role of miR-142 in the heart, as well as to identify potential direct targets, the gene expression profiles of cardiac myocytes were examined with miR-142 gain (comparing miR-142 and NT lentivirus-transfected cells). Significantly regulated genes were analyzed and potential targets were identified by reciprocal regulation with miR-142 loss (cells transduced with miR-142-5p and -3p antisense inhibitors or a non-silencing oligonucleotide). The direction of change was validated in each condition by QPCR in a subset of 26 genes. Gene Ontology analysis identified several growth-associated pathways and functions (angiogenesis, hypertrophy, and muscle contraction) among the differentially regulated genes, including gp130/IL6st, NF-kappaB1, NFkappaB2, p300 and alpha-actinin. To confirm the prediction that miR-142 would affect cell growth or sarcomere assembly, NRVM were transduced as above to achieve gain or loss of both miR-142-5p and 3p, followed by immunostaining with antibodies directed against GATA4, α-myosin heavy chain, F-actin and pan-α-actinin. Neither intervention had a visible effect in cell size or on GATA4, myosin or sarcomeric actin staining. However, α-actinin was markedly depleted in cells expressing the miR-142 lentivirus. This result was confirmed by immunoblot in total cell lysates, indicating almost total absence of actinin in the fraction of virally transduced cells.

Two major isoforms of α-actinin are expressed in the heart, a actinin 2 (Actn2) and a actinin 4 (Actn4). TargetScan and PITA algorithms predicted miR-142-5p binding sites in both isoforms; the ACTN4 site is conserved in mouse, rat and humans. Of note, neither ACTN2 nor ACTN4 mRNAs were differentially expressed in the microarray assays, suggesting that miR-142 might target protein translation rather than transcript stability. Mutation of the miR-142 binding site in the α-actinin 4 3'UTR, and luciferase constructs containing either the wt or mutant 3'UTR were expressed in the presence of miR-142-5p or a scrambled sequence. MiR-142-5p significantly repressed the wt but not the mutant 3'UTR-containing vector. No repression of either vector was seen with the scrambled sequence, indicating that this α-actinin isoform is a direct, specific target of miR-142-5p.

miR-142 globally represses cytokine signaling. A striking effect of miR-142 overexpression was the apparent suppression of multiple components of immune signaling in chemokine and cytokine signal transduction pathways. Of 91 differentially regulated genes within these GO functions, 69 were strongly repressed by miR-142 gain, and of 26 tested, almost all were correspondingly upregulated with miR-142 loss (Table 5). This global repression of cytokine genes was accompanied by a marked functional loss of signaling through the TNF-α-NFkB pathway. Macrophage-derived cytokines, including interleukin 1-β (IL1β), tumor necrosis factor (TNFα), and interferon gamma (IFNγ), are powerful activators of inducible nitric oxide synthase (iNOS) transcription in cardiac myocytes and in many other cell types. NRVM was exposed to a mixture of these cytokines after transduction with either miR-142 or NT lentiviruses and monitored iNOS mRNA levels by QPCR and NO production as reflected in media nitrite levels. As expected, cardiac myocytes expressing the non-targeting sequence produced high levels of both iNOS and NO within 48 hours after cytokine exposure, while NRVM expressing miR-142 induced only half as much iNOS and NO under the same conditions. Since lentiviral transduction was only ~50% efficient in these experiments as estimated by RFP expression, this result is effectively consistent with elimination of the cytokine response in miR-142-transduced myocytes.

IL6st is a direct target of miR-142. Several of the differentially regulated genes identified by microarray were predicted to be direct targets; in particular, the interleukin receptor IL6st, previously shown to be critical for survival signaling in the myocardium had potential 3'UTR binding sites for both miR-142-5p and -3p. A luciferase construct containing the IL6st 3'UTR, but not a mutant 3'UTR lacking both sites, was strongly repressed by miR-142 but not by the NT sequence. These findings confirm that IL6st is a direct target of either or both miR-142-5p and -3p.

Forced expression of miR-142 suppresses p300 and reverses p300-driven cytokine gene expression. The above findings indicate that miR-142 inhibits at least 2 signal pathways that are critical to hypertrophic growth in vivo and suggest that its downregulation is essential for adaptive growth. To further investigate this, the miR-142- and non-targeting lentiviral vectors were transduced into newborn wt mice and littermates carrying a p300 myocyte-specific transgene. As previously reported, these p300tg mice develop initial hypertrophy followed by heart failure within the first 6 months of life. Expression analysis of the myocardium at 2 months confirmed miR-142 overexpression in all animals transduced with miR-142 (both wt and p300tg). Cytokine pathway gene expression was assayed at 2 months using a custom high density qPCR array representing the differentially regulated immune response genes previously identified in cell culture, as well as other predicted targets of miR-142 (Table 6). Both p300 and IL6st mRNA levels were reduced in myocardium of mice receiving miR-142, confirming our in vitro results (Table 6). For most genes, the direction of change was similar to that seen in cultured myocytes; changes in 16 of 94 genes were significant with nominal p values <0.05 in either the wt or p300tg backgrounds. Of the 16, 11 were downregulated. Interestingly, the 5 upregulated genes each encode proteins with immune inhibitory function: Itgam and Itgb2 encoding integrin beta-2/alpha-M; two members of the Ikappa B family, Nfkbia and Nfkbil 1; and the prostaglandin F-2-alpha receptor inhibitor Ptgfrn. Significantly, mice expressing the p300 transgene had an altered immune response gene expression profile that was partially normalized by expression of miR-142 (Table 6). These results indicate that miR-142 opposes the actions of p300 in vivo, either through negative regulation of p300 itself, or by direct effect on genes downstream of p300. Furthermore, upregulation of miR-142 is associated with an immune suppression gene profile.

Forced expression of miR-142 during postnatal growth induces apoptosis and heart function. The changes in gene expression enforced by miR-142 were associated with significant impact on heart structure and function in both wt and p300tg mice. All miR-142 recipients had reduced LV ejection fraction, fractional shortening, and increased systolic and diastolic dimensions relative to their NT-injected, genotype-matched controls (FIGS. 2A and B), indicative of development or worsening of heart failure. Pathologic analysis confirmed LV chamber dilatation of the miR-142-transduced hearts (FIG. 2C). Microscopic evaluation revealed abundant myocyte apoptosis in miR-142-transduced LV from both genotypes; in contrast, apoptosis was absent or very rare in NT-transduced hearts (FIG. 2D).

Figure 2:
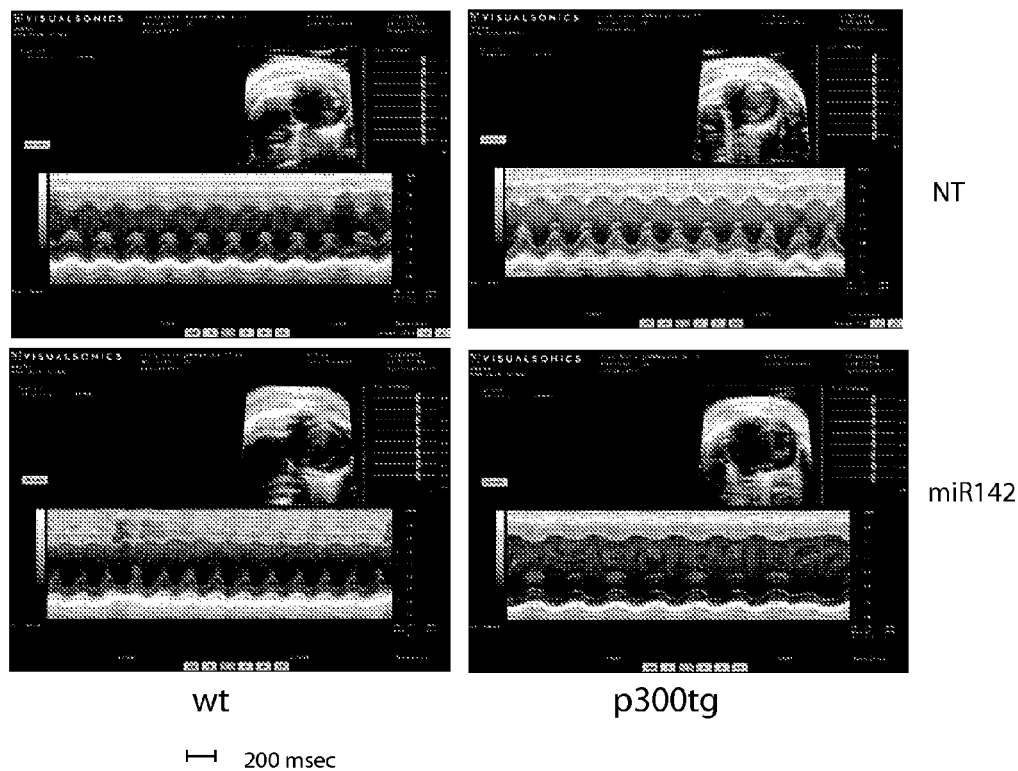
FIG. 2 shows that forced expression of miR-142 impairs cardiac function during postnatal growth. 5-day old wt and p300tg pups were transduced with the indicated lentiviruses (total dose $10^8$ viral particles/pup), and evaluated at 2 months of age. A. Cardiac contractile function assessment. Representative echocardiographic images showing M-mode and 2D sectors for each genotype and condition. B. Altered LV systolic function and p300-dependent myocardial growth induced by miR-142-5p/-3p. Left ventricular ejection fraction (LVEF) and internal dimensions in systole and diastole (LVIDs and LVIDd) are shown for all groups. N=5-8 animals per group. *p<0.05, **p<0.01. See Supplementary Table IV for summary of all parameters. C. Representative 4 chamber sections of wt and p300tg hearts treated with miR-142 or NT vectors. LV tissue from 2.5 mo old mice was formalin-fixed, paraffin-embedded and stained with hematoxylin and eosin. Original magnification: 1λ. D. MiR-142 induces myocardial apoptosis. LV myocardium was examined for apoptotic cells using TUNEL (Left) Representative images. TUNEL+ nuclei are stained blue. Original magnification: ×60. (Right) TUNEL+ nuclei were quantitated in 10 randomly chosen fields per section in each of 5 hearts per condition. E and F. Rescue of p300-induced cardiac dysfunction by anti-miR-142-5p/-3p. (E) representative 2D and M-mode images. F. Quantitation of LV ejection fraction (LVEF) and systolic and diastolic dimensions (LVIDs and LVIDd) are shown for all groups. N=3-6 animals per group. *p<0.05, **p<0.01.
Figure 2:
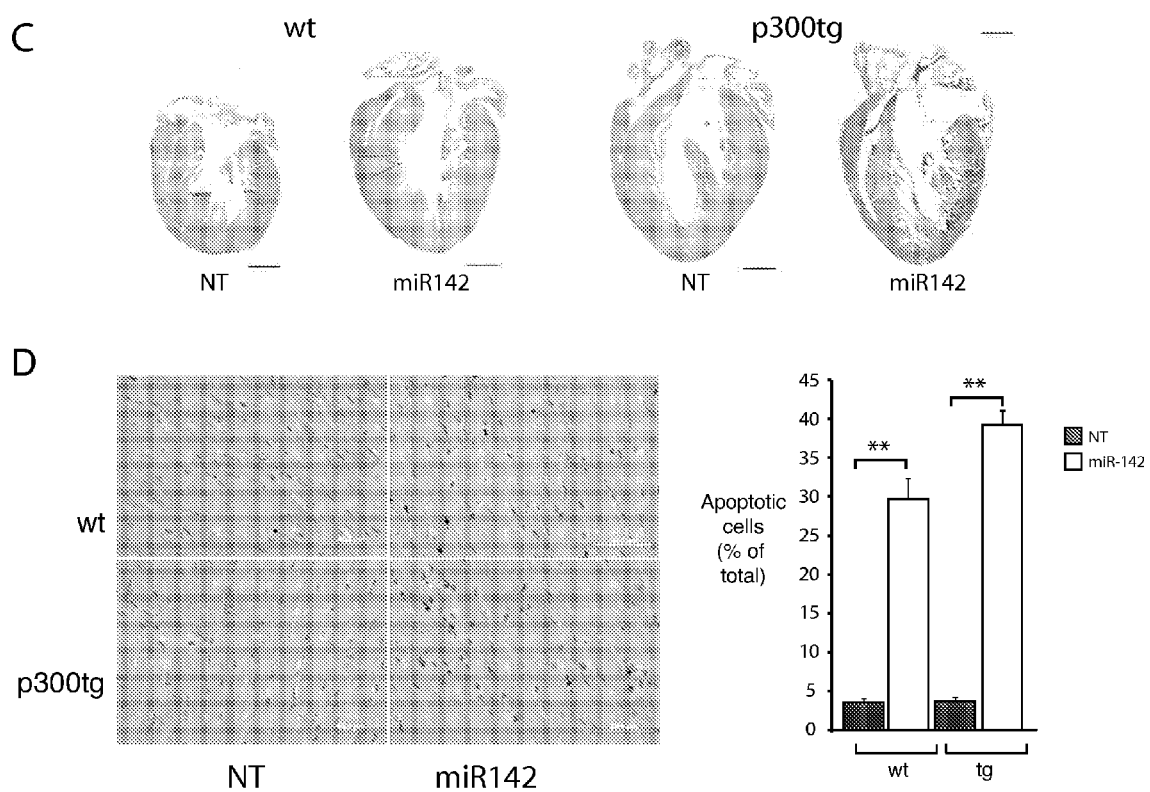
Figure 2:
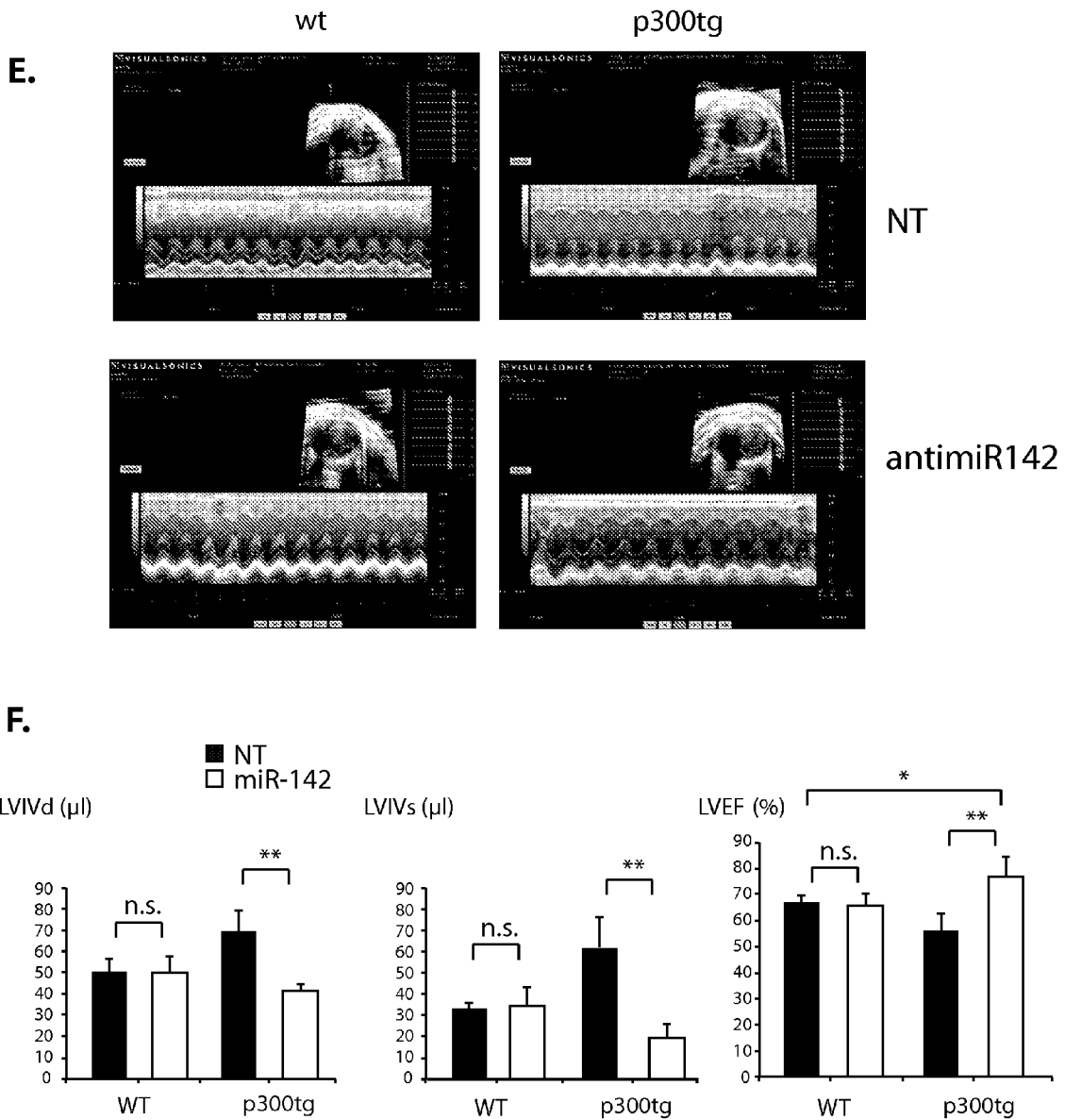
Figure 3:
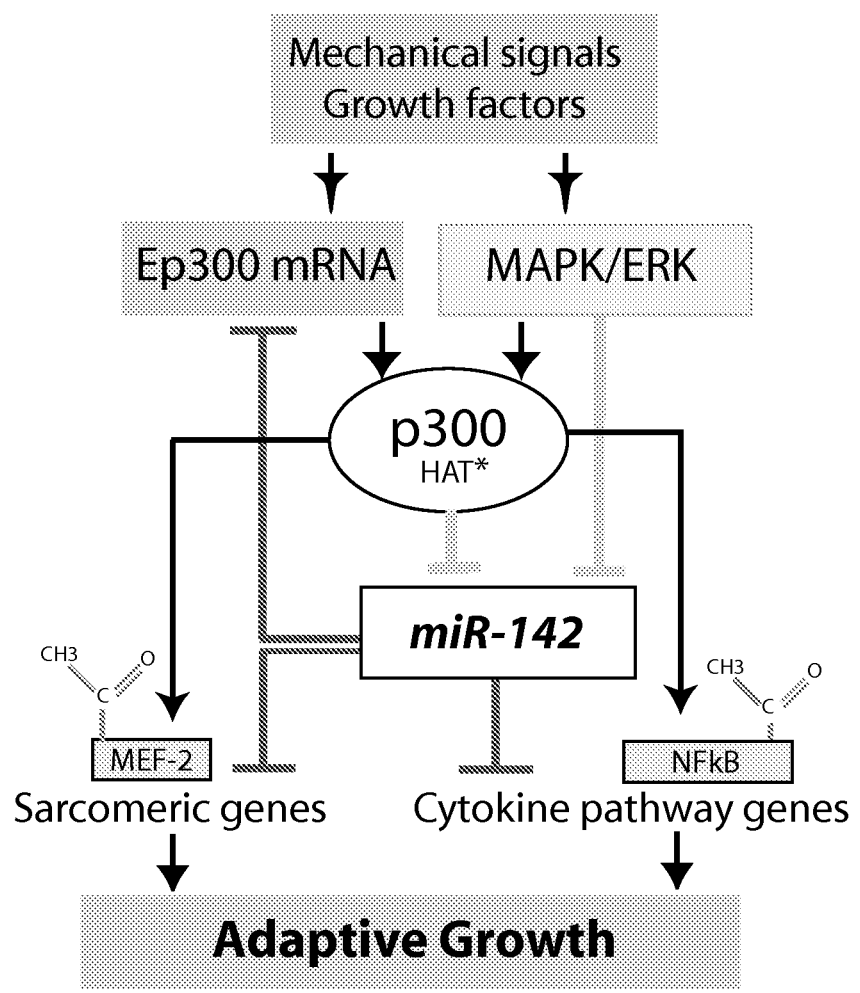
FIG. 3 is a model of a mutual inhibitory loop involving p300 and miR-142 that controls cytokine signaling in cardiac myocyte growth. Mechanical and other trophic signals activate MAP kinases, which phosphorylate and activate p300 acetyltransferase; p300 acetylates transcription factors, including MEF2 and NFkB, that promote hypertrophic growth. At the same time, MAPK and p300 suppress expression of miR-142-5p and 3p, through unknown shared or distinct mechanisms. Loss of miR-142 removes a brake to the further induction of genes required for myocyte growth, especially those in survival pathways associated with cytokine signaling.

Antisense inhibition of miR-142 rescues heart function in p300 transgenic mice. A similar approach was used to assess the effects of depleting the already low levels of miR-142 in wildtype and p300tg juvenile mice, transducing neonatal pups with miR-142 antisense-encoding and non-targeting lentiviral vectors and determining cardiac function by echocardiography at 2 months. Non-targeting- and antisense-transduced wt mice were functionally indistinguishable (FIG. 2 E, F). However, a remarkable rescue effect of miR-142 loss was observed in the p300tg mice. p300tg mice transduced with the control lentivirus already display mild systolic dysfunction at 2 months of age (see also FIG. 2A, B). Depletion of residual miR-142 not only restored myocardial function to normal but improved it over wt function as determined by multiple measures (chamber volumes, fractional shortening, ejection fraction; FIG. 2F). These results strongly support the adaptive value of miR-142 downregulation during cardiac growth, and suggest the critical importance of the cytokine milieu in determining adaptive cardiac hypertrophy. It is envisioned that under basal conditions, miR-142-5p maintains p300 at low levels through direct targeting of it mRNA (FIG. 3).

These results have implications for the clinical use of compounds that alter p300 activity or expression, particularly histone deacetylase inhibitors (Stiehl et al., Cancer Res 67, 2256-2264 (2007)). Furthermore, given the powerful and broad effects of miR-142 on cytokine signaling, it may represent a therapeutic target in a number of diseases, including heart failure, inflammation and cancer.

TABLE 4

Cytokine pathway genes differentially regulated in cardiac myocytes over-expressing miR-142

| | Gene Name | Description | Fold change (miR142 vs non target) | P value |
|---|---|---|---|---|
| 1 | Il1a | Interleukin-1 alpha precursor (IL-1 alpha). | 0.209506591 | 0 |
| 2 | Il1b | Interleukin-1 beta precursor (IL-1 beta). | 0.34885606 | 0 |
| 3 | Il6 | Interleukin-6 precursor (IL-6). | 0.560865416 | 0.00006 |
| 4 | Il7 | Interleukin-7 precursor (IL-7). | 0.365077684 | 0.00003 |
| 5 | Il10 | Interleukin-10 precursor (IL 10) (Cytokine synthesis inhibitory factor) (CSIF). | 2.399502107 | 0.00035 |

TABLE 4-continued

Cytokine pathway genes differentially regulated in cardiac myocytes over-expressing miR-142

| | Gene Name | Description | Fold change (miR142 vs non target) | P value |
|---|---|---|---|---|
| 6 | Il12a | Interleukin-12 subunit alpha precursor (IL-12A)(IL-12 subunit p35)(Cytotoxic lymphocyte maturation factor 35 kDa subunit)(CLMF p35). | 2.073081875 | 0.0061 |
| 7 | Il1r1 | Interleukin-1 receptor type I precursor (IL-1R-1) (p80) (CD121a antigen). | 0.460860024 | 0.00002 |
| 8 | Il1rl1 | Interleukin-1 receptor-like 1 precursor (Fos-responsive gene 1 protein) (Fit-1). | 2.911534265 | 0.00001 |
| 9 | Irf1 | Interferon regulatory factor 1 (IRF-1). | 0.355296339 | 0 |
| 10 | Ccl3 | Small inducible cytokine A3 precursor (CCL3) (Macrophage inflammatory protein 1-alpha) (MIP-1-alpha). | 0.756729855 | 0.03603 |
| 11 | Ccl19 | PREDICTED: similar to EBI-1 ligand chemokine | 0.404626946 | 0.00009 |
| 12 | Ccl2 | Small inducible cytokine A2 precursor (CCL2) (Monocyte chemotactic protein 1) (MCP-1) (Monocyte chemoattractant protein 1) (Immediate-early serum-responsive JE protein). | 0.56630944 | 0.00022 |
| 13 | Ccl5 | Small inducible cytokine A5 precursor (CCL5) (T-cell-specific RANTES protein) (SIS-delta). | 0.127737736 | 0 |
| 14 | Ccr5 | C-C chemokine receptor type 5 (C-C CKR-5) (CC-CKR-5) (CCR-5) (MIP-1 alpha receptor) (CD195 antigen). | 5.944670173 | 0.00001 |
| 15 | Cxcl10 | Small inducible cytokine B10 precursor (CXCL10) (Interferon inducible protein 10) (Gamma-IP10) (IP-10) (MOB-1 protein). | 0.272392459 | 0 |
| 16 | Cxcl11 | chemokine (C—X—C motif) ligand 11 | 0120954186 | 0 |
| 17 | Cxcl3 | Macrophage inflammatory protein 2-beta precursor (MIP2-beta) (CINC-2-beta). | 0.32 | 0.0000 |
| 18 | Cxcl9 | small inducible cytokine B9 [Source: RefSeq_peptide; Acc: NP_6637051 | 0.25 | 0.0000 |
| 19 | Cxcl1 | Growth regulated alpha protein precursor (CXCL1) (Cytokine-induced neutrophil chemoattractant) (CINC-1) (Platelet-derived growth factor-inducible protein KC). | 0.37 | 0.0000 |
| 20 | Cxcl2 | Macrophage inflammatory protein 2 precursor (MIP2) (CINC-3).] | 0.45 | 0.0002 |
| 21 | Cxcl6 | Small inducible cytokine B5 precursor | 0.45 | 0.0001 |
| 22 | Csf1 | Macrophage colony-stimulating factor 1 precursor (CSF-1) (MCSF | 0.670749065 | 0.00607 |
| 23 | Csf2 | Granulocyte-macrophage colony-stimulating factor (GM-CSF) (Colony-stimulating factor) (CSF). | 0.4107022 | 0.00001 |
| 24 | Csf3 | Colony stimulating factor 3 | 0.707309586 | 0.02245 |
| 25 | Stat3 | Signal transducer and activator of transcription 3 | 0.634453401 | 0.00102 |

TABLE 4-continued

Cytokine pathway genes differentially regulated in cardiac myocytes over-expressing miR-142

| | Gene Name | Description | Fold change (miR142 vs non target) | P value |
|---|---|---|---|---|
| 26 | Gbp1 | PREDICTED: similar to guanylate binding protein 1, interferon-inducible, 67 kDa | 0.40875299 | 0 |
| 27 | Ifih1 | Interferon induced with helicase C domain 1 | 0.25113638 | 0 |
| 28 | Ifi47 | Interferon gamma inducible protein | 0.363570944 | 0 |
| 29 | Nfkbil1 | NF-kappa β inhibitor-like protein 1 (Inhibitor of kappa β-like) (1-kappa β-like)(Nuclear factor of kappa light polypeptide gene enhancer in β-cells inhibitor-like 1). | 0.46 | 0.0003 |
| 30 | Nfkb1 | Nuclear factor NF-kappa-β p105 subunit (DNA-binding factor KBF1) (EBP-1) [Contains: Nuclearfactor NF-kappa-β p50 subunit/ (Fragment). | 0.578544257 | 0.0001 |
| 31 | Nfkb2 | Nuclear factor of kappa light polypeptide gene enhancer in B-cells 2 (p49/p100) | 0.458114911 | 0.00008 |
| 32 | Nfkbia | NF-kappa β inhibitor alpha (1-kappa-β-alpha) (Ikappaβalpha) (IKβ-alpha) (RL/IF-1). | 0.543429566 | 0.00005 |
| 33 | Rela | v-rel reticuloendotheliosis viral oncogene homolog A | 0.628016289 | 0.00084 |
| 34 | Nos2 | Nitric oxide synthase, inducible (EC 1.14.13.39) NOS type II) (Inducible NO synthase) (Inducible NOS) (INOS) | 0.179610839 | 0 |
| 35 | Cd3eap | CD3E antigen, epsilon polypeptide associated protein | 0.691435375 | 0.0024 |
| 36 | Cd8a | T-cell surface glycoprotein CD8 alpha chain precursor (CD8 antigen 32 kDa chain) (OX-8 membrane antigen) (CD8a antigen). | 1.611094939 | 0.00839 |
| 37 | Cd28 | T-cell specific surface glycoprotein CD28 precursor | 0.124313835 | 0 |
| 38 | Cd38 | ADP-ribosyl cyclase 1 (EC 3.2.2.5) (Cyclic ADP-ribose hydrolase 1) (cADPr hydrolase 1) (CD38H). | 2.011787569 | 0.00048 |
| 39 | Cd80 | CD90 antigen | 0.561359588 | 0.00036 |
| 40 | Nr3c1 | Glucocorticoid receptor (GR) | 0.236619912 | 0 |
| 41 | Irg1 | immunoresponsive gene 1 | 0.207772334 | 0 |
| 42 | Itgb2 | Itgb2 protein | 2.687368836 | 0.00002 |
| 43 | Hpgd | 15-hydroxyprostaglandin dehydrogenase | 2.879424222 | 0.00253 |
| 44 | Ptger3 | Prostaglandin E2 receptor, EP3 subtype (Prostanoid EP3 receptor) (PGE receptor, EP3 subtype). | 2.475717535 | 0.00005 |
| 45 | Ptgfrn | Prostaglandin F2 receptor negative regulator precursor (Prostaglandin F2-alpha receptor regulatory protein) (Prostaglandin F2-alpha receptor-associated protein) (CD315 antigen). | 2.141031532 | 0.0005 |
| 46 | Ptgs2 | Prostaglandin G/H synthase 2 precursor (EC 1.14.99.1) (Cyclooxygenase-2) (COX-2) (Prostaglandin-endoperoxide synthase 2) (Prostaglandin H2 synthase 2) (PGH synthase 2) | 0.497660021 | 0.00061 |

TABLE 4-continued

Cytokine pathway genes differentially regulated in cardiac myocytes over-expressing miR-142

| | Gene Name | Description | Fold change (miR142 vs non target) | P value |
|---|---|---|---|---|
| 47 | Icam1 | Intercellular adhesion molecule 1 precursor (ICAM-1). | 0.504979379 | 0.00003 |
| 48 | Selp | P-selectin precursor (Granule membrane protein 140) (GMP-140) (PADGEM) (Leukocyte-endothelial cell adhesion molecule 3) (LECAM3) (CD62P antigen). | 2.310793611 | 0.00029 |
| 49 | Hmox1 | Heme oxygenase 1 (EC 1.14.99.3) (HO-1) (HSP32). | 0.70753948 | 0.00427 |
| 50 | Pla2g5 | Calcium-dependent phospholipase A2 precursor (EC 3.1.1.4) (Phosphatidylcholine 2-acylhydrolase) (PLA2-10) | 2.324124101 | 0 |
| 51 | Pla2g7 | phospholipase A2, group VII (platelet-activating factor acetylhydrolase, plasma) (predicted) | 1.959731112 | 0.00085 |
| 52 | Mapk1 | Mitogen-activated protein kinase 1 (EC 2.7.11.24) (Extracellular signal-regulated kinase 2) (ERK-2) (Mitogen-activated protein kinase 2) (MAP kinase 2) (MAPK2) (p42-MAPK) (ERT1). | 2.279910323 | 0.00021 |
| 53 | Itgam | integrin alpha M | 1.902868338 | 0.00056 |
| 54 | Tgfb1 | Transforming growth factor beta-1 precursor (TGF-beta-1) [Contains: Latency-associated peptide (LAP)]. | 3.042151047 | 0.00005 |
| 55 | Smad7 | Mothers against decapentaplegic homolog 7 (SMAD 7) (Mothers against DPP homolog 7) (Smad7). | 0.734469233 | 0.01223 |
| 56 | Skil | PREDICTED: similar to proto-oncogene, FL isoform | 0.25443186 | 0 |
| 57 | Ltc4s | leukotriene C4 synthase | 1.945892352 | 0.00238 |
| 58 | Tnf | Tumor necrosis factor precursor (TNF-alpha) (Tumor necrosis factor ligand superfamily member 2) (TNF-a) (Cachectin) [Contains: Tumor necrosis factor, membrane form; Tumor necrosis factor, soluble form]. | 0.180104475 | 0 |
| 59 | Pla2g2a | Phospholipase A2, membrane associated precursor (EC 3.1.1.4) (Phosphatidylcholine 2-acylhydrolase) (Group IIA phospholipase A2) (GIIC sPLA2). | 0.527461223 | 0.0011 |
| 60 | Pla2g2d | phospholipase A2, group IID | 1.987710139 | 0.00701 |
| 61 | Vegfa | Vascular endothelial growth factor A precursor (VEGF-A) (Vascular permeability factor) (VPF). | 0.420143357 | 0 |
| 62 | Vcam1 | Vascular cell adhesion protein 1 precursor (V-CAM1). | 0.390603199 | 0 |

TABLE 4-continued

Cytokine pathway genes differentially regulated in cardiac myocytes over-expressing miR-142

| | Gene Name | Description | Fold change (miR142 vs non target) | P value |
|---|---|---|---|---|
| 63 | Tnfrsf12a | tumor necrosis factor receptor superfamily, member 12a | 0.41 | 0.0000 |
| 64 | Tnfsf18 | tumor necrosis factor (ligand) superfamily, member 18 | 2.17 | 0.0000 |
| 65 | Tnfrsf1b | Tumor necrosis factor receptor superfamily member 1B precursor (Tumor necrosis factor receptor 2) (TNF-R2) (Tumor necrosis factor receptor type II) (p75) (p80 TNF-alpha | 0.48 | 0.0007 |
| 66 | Traf3ip1 | TNF receptor-associated factor 3 interacting protein 1 (predicted) | 0.391924491 | 0.00016 |
| 67 | Traf6 | Tnf receptor-associated factor 6 | 0.633678805 | 0.0127 |
| 68 | Trafd1 | Fln29 | 0.492285788 | 0.00001 |
| 69 | Traf2 | Tnf receptor-associated factor 2 | 0.31 | 0.0000 |
| 70 | Traf3 | PREDICTED: similar to CD40 receptor associated factor 1 | 0.285009975 | 0 |
| 71 | Agtr1a | Type-1A angiotensin II receptor (AT1) (AT1A) | 1.43605624 | 0.0034 |
| 72 | Tbxas1 | Thromboxane-A synthase (EC 5.3.99.5) (TXA synthase) (TXS) (Cytochrome P4505A1). | 3.931189275 | 0.00001 |
| 73 | Lifr | Leukemia inhibitory factor receptor precursor (LIF receptor) (LIF-R) (CD118 antigen). | 0.482319206 | 0.00022 |
| 74 | Tbxa2r | Thromboxane A2 receptor (TXA2-R) (Prostanoid TP receptor) (TXR2). | 1.942212887 | 0.00022 |
| 75 | Nfatc4 | PREDICTED. similar to Cytoplasmic nuclear factor of activated T-cells 4 | 0.524577729 | 0.00011 |
| 76 | Pf4 | Platelet factor 4 precursor (PF-4) (CXCL4). | 1.45510906 | 0.02818 |
| 77 | Socs1 | Suppressor of cytokine signaling 1 (SOCS-1). | 0.527788334 | 0.00005 |
| 78 | Socs5 | PREDICTED: similar to Suppressor of cytokine signaling 5 | 0.648074703 | 0.00046 |
| 79 | Socs4 | PREDICTED: similar to suppressor of cytokine signalling 4 | 0.179610839 | 0 |
| 80 | Tfrc | PREDICTED: similar to RIKEN cDNA A930038C07 | 0.304601469 | 0 |
| 81 | Actb | Actin, cytoplasmic 1 (Beta-actin). | 2.456664597 | 0 |
| 82 | Ifnb1 | Interferon beta precursor (IFN-beta). | 0.038298762 | 0 |
| 83 | Ifna4 | PREDICTED: similar to alpha-interferon | 0.372604156 | 0.00005 |
| 84 | Birc3 | Inhibitor of apoptosis protein 1 | 0.395367791 | 0.00002 |
| 85 | Map3k14 | PREDICTED: similar to NF-kappaB inducing kinase | 0.426619637 | 0.00213 |
| 86 | Fkbp5 | FK506 binding protein 5 (predicted) | 0.219754354 | 0 |
| 87 | Ptpn11 | Tyrosine-protein phosphatase non-receptor type 11 (EC 3.1.3.48) (Protein-tyrosine phosphatase SYP) (PTP-1D) (SH-PTP2) (SHP-2) (Shp2). | 0.23791635 | 0 |

TABLE 4-continued

Cytokine pathway genes differentially regulated in cardiac myocytes over-expressing miR-142

| | Gene Name | Description | Fold change (miR142 vs non target) | P value |
|---|---|---|---|---|
| 88 | Nr2c2 | Orphan nuclear receptor TR4. | 0.316680761 | 0 |
| 89 | Map3k2 | Mitogen activated serine/threonine protein kinase MEKK2 (Fragment). | 0.204045091 | 0 |
| 90 | Map3k6 | PREDICTED: similar to apoptosis signal-regulating kinase 2 | 0.61335713 | 0.00123 |
| 91 | Ptpn4 | Protein tyrosine phosphatase non-receptor type 4 (Fragment). | 0.42408865 | 0.00002 |
| 92 | Ptpn9 | protein tyrosine phosphatase, non-receptor type 9 | 0.665271387 | 0.00225 |
| 93 | Bdkrb1 | B1 bradykinin receptor (BK-1 receptor) (B1R) (Kinin B1 receptor) (KB1). | 0.281553931 | 0 |
| 94 | Igsf1 | immunoglobulin superfamily, member 1 | 1.964491723 | 0.0002 |

TABLE 5

Expression levels of immune response genes in miR142- or NT-transduced (control) wt and p300tg mouse hearts at 2 months. Shading = nominally significant (p <0.05) differential regulation by miR-142 in either or both wt and p300tg mice. n = 3 per condition.

| | Gene Symbol-ABI Assay ID | Average absolute values (N = 6) wt-ctrl | Average absolute value (N = 6) wt-mir142 | P VALUE wt-ctrl vs wt-miR142 | Average absolute value (N = 4) p300-tg-ctrl | Average absolute value (N = 4) p300-tg-mir142 | P value tg-ctrl vs tg-miR142 |
|---|---|---|---|---|---|---|---|
| 1 | Il6st | 6235180. | 3518022. | 0.00041788 | 7656923. | 4044416.09 | 0.46250063 |
| 2 | Actb | 62634.4 | 1124355. | 0.24677317 | 1290.1 | 1714.7 | 0.94283152 |
| 3 | Agtr1a | 2828.5 | 2963.7 | 0.87258953 | 3663.5 | 2233.4 | 0.08988724 |
| 4 | Bdkrb 1 | 470.3 | 386.8 | 0.86863822 | 19639.9 | 1281.0 | 0.30715901 |
| 5 | Birc3 | 1195.7 | 1216.5 | 0.98642803 | 384.3 | 128.8 | 0.72457154 |
| 6 | Ccl19 | 59.1 | 53.9 | 0.85263048 | 72.8 | 126.9 | 0.42502378 |
| 7 | Ccl2 | 550.5 | 326.5 | 0.03892318 | 1807.8 | 1214.6 | 0.07466506 |
| 8 | Ccl3 | 46.6 | 26.3 | 0.26453123 | 72.2 | 100.5 | 0.08019658 |
| 9 | Ccl5 | 271.5 | 290.2 | 0.84692828 | 452.7 | 429.9 | 0.88904811 |
| 10 | Ccr5 | 426.9 | 210.3 | 0.09017316 | 546.8 | 470.4 | 0.88904811 |
| 11 | Cd28 | 200.0 | 39.4 | 0.21414379 | 25311.4 | 197.7 | 0.01758901 |
| 12 | Cd38 | 3553.4 | 3670.3 | 0.94177028 | 6760.9 | 9449.4 | 0.32584597 |
| 13 | Cd3eap | 4536.4 | 1173.6 | 0.32612337 | 24512257. | 10552.2 | 0.03087354 |
| 14 | Cd80 | 71.8 | 65.4 | 0.76790433 | 260.4 | 427.9 | 0.05293970 |
| 15 | Cd8a | 38.9 | 43.8 | 0.79857586 | 63.1 | 63.3 | 0.99815809 |
| 16 | Csf1 | 8235.6 | 5481.4 | 0.19051916 | 17059.1 | 14935.9 | 0.40381962 |
| 17 | Csf2 | 1.2 | 18.1 | 0.06237071 | 4.6 | 2.8 | 0.67104471 |

TABLE 5-continued

Expression levels of immune response genes in miR142- or NT-transduced (control) wt and p300tg mouse hearts at 2 months. Shading = nominally significant (p <0.05) differential regulation by miR-142 in either or both wt and p300tg mice. n = 3 per condition.

| 18 | Csf3 | 8.0 | 6.5 | 0.84256030 | 5.3 | 8.9 | 0.71471865 |
|---|---|---|---|---|---|---|---|
| 19 | Cxcl10 | 147.1 | 133.5 | 0.82262502 | 354.8 | 507.5 | 0.23997377 |
| 20 | Cxcl11 | 28.6 | 41.2 | 0.62065547 | 30.7 | 21.4 | 0.69274649 |
| 21 | Cxcl1 | 133.9 | 122.1 | 0.75628242 | 187.4 | 217.5 | 0.31938411 |
| 22 | Cxcl2 | 14.5 | 15.4 | 0.88384770 | 35.1 | 48.8 | 0.21635850 |
| 23 | Cxcl3 | 280.3 | 3.9 | 0.21669982 | 15.6 | 17.8 | 0.94742950 |
| 24 | Cxcl5 | 91.4 | 80.5 | 0.72107681 | 80.6 | 87.8 | 0.77736875 |
| 25 | Cxcl9 | 340.7 | 431.0 | 0.45296999 | 890.4 | 1075.7 | 0.57411639 |
| 26 | Fkbp5 | 3342.4 | 3385.1 | 0.99100258 | 291.8 | 1350.7 | 0.50672035 |
| 27 | Gbp1 | 16.9 | 11.6 | 0.79521858 | 783.6 | 1.9 | 0.00077119 |
| 28 | Hmox1 | 1608.3 | 2737.9 | 0.35649143 | 2883.3 | 2792.3 | 0.92348285 |
| 29 | Hpgd | 1363.1 | 1009.7 | 0.56523901 | 1745.6 | 1170.0 | 0.72610905 |
| 30 | Icam1 | 3905.6 | 8850.2 | 0.06902203 | 318.6 | 4537.7 | 0.25330709 |
| 31 | Ifi47 | 1395.8 | 1018.1 | 0.46300839 | 6561.2 | 4119.5 | 0.16761037 |
| 32 | Ifih1 | 1041.9 | 1024.1 | 0.96411137 | 7161.3 | 7848.8 | 0.70892086 |
| 33 | Ifna4 | 133.3 | 101.8 | 0.84648391 | 29.0 | 18.6 | 0.87862367 |
| 34 | Ifnb1 | 33.0 | 139.0 | 0.32615296 | 146.0 | 36827.6 | 0.11957728 |
| 35 | Igsf1 | 176.7 | 97.3 | 0.19991244 | 112.2 | 58.5 | 0.75120556 |
| 36 | Il1 | 29.4 | 3.6 | 0.01796991 | 12.9 | 9.2 | 0.83140177 |
| 37 | Il12a | 50.2 | 67.3 | 0.80210509 | 6.7 | 6.4 | 0.96823842 |
| 38 | Il1a | 14.3 | 4.4 | 0.12968732 | 6.1 | 3.6 | 0.69233960 |
| 39 | Il1 | 174.9 | 183.5 | 0.88286242 | 259.3 | 383.7 | 0.36938232 |
| 40 | Il1r1 | 1454.2 | 1104.1 | 0.39343630 | 1660.9 | 2040.2 | 0.51169980 |
| 41 | Il1rl1 | 77.3 | 83.3 | 0.80689004 | 104.7 | 87.6 | 0.37515401 |
| 42 | Il6 | 11.2 | 7.2 | 0.35809890 | 23.1 | 86.3 | 0.28377431 |
| 43 | Il7 | 178.9 | 49.9 | 0.20200275 | 217.2 | 1893.4 | 0.60466295 |
| 44 | Irf1 | 4733.4 | 4275.4 | 0.76015094 | 7307.9 | 5842.0 | 0.28258364 |
| 45 | Irg1 | 22.1 | 7.1 | 0.23060731 | 690.7 | 39.7 | 0.05784595 |
| 46 | Itgam | 10.3 | 21.4 | 0.47351384 | 50.5 | 370.7 | 0.03489134 |
| 47 | Itgb2 | 884.2 | 945.5 | 0.88170628 | 1151.3 | 3769.7 | 0.03489134 |
| 48 | Lifr | 12043. | 12498. | 0.92783324 | 17575. | 12171. | 0.17033719 |
| 49 | Ltc4s | 1115.4 | 807.7 | 035797654 | 2023.0 | 1327.0 | 0.23624173 |
| 50 | Map3k | 22119. | 729.1 | 0.19154770 | 490.6 | 6.9 | 0.47912689 |
| 51 | Map3k | 736.1 | 218.2 | 0.40981131 | 2156.5 | 112.4 | 0.02474311 |
| 52 | Map3k | 804.9 | 866.6 | 0.91569393 | 4858.3 | 433.5 | 0.27939032 |
| 53 | Mapk1 | 13173. | 12333. | 0.82052701 | 16742. | 13765. | 0.15609664 |

TABLE 5-continued

Expression levels of immune response genes in miR142- or NT-transduced (control) wt and p300tg mouse hearts at 2 months. Shading = nominally significant (p <0.05) differential regulation by miR-142 in either or both wt and p300tg mice. n = 3 per condition.

| | | | | | | | |
|---|---|---|---|---|---|---|---|
| 54 | Nfatc4 | 156.9 | 48.6 | 0.31524717 | 2926.1 | 30.7 | 0.08909666 |
| 55 | Nfkb1 | 1134.9 | 6489.2 | 0.338399 | 3750.8 | 9485.4 | 0.09300693 |
| 56 | Nfkb2 | 465.1 | 2414.2 | 0.31419756 | 57419. | 63688. | 0.85834581 |
| 57 | Nfkbia | 13688. | 23106. | 0.30640681 | 8383.0 | 45097. | 0.03030037 |
| 58 | Nfkbil | 31831. | 3540.3 | 0.36361972 | 14.7 | 1626.4 | 0.03342276 |
| 59 | Nos2 | 246.9 | 1034.8 | 0.34027465 | 152.9 | 2877.8 | 0.18836402 |
| 60 | Nr2c2 | 2424.3 | 2021.0 | 0.76316909 | 42.3 | 214.1 | 0.61138350 |
| 61 | Nr3c1 | 4790.1 | 7227.8 | 0.34863626 | 5503.9 | 21350. | 0.08050282 |
| 62 | Pf4 | 15081. | 14463. | 0.94788692 | 171.3 | 170.6 | 0.99876215 |
| 63 | Pla2g2 | 49.0 | 38.2 | 0.95921419 | 53.5 | 212.9 | 0.8563179 |
| 64 | Pla2g2 | 171.8 | 261.8 | 0.28710138 | 377.0 | 391.9 | 0.89378640 |
| 65 | Pla2g5 | 3102.0 | 3070.3 | 0.97178807 | 3243.3 | 1689.3 | 0.09130000 |
| 66 | Pla2g7 | 1072.1 | 899.8 | 0.63712007 | 1490.7 | 1180.6 | 0.11602161 |
| 67 | Ptger3 | 163.8 | 62.5 | 0.10634754 | 280.5 | 528.4 | 0.77256498 |
| 68 | Ptgfrn | 4733.4 | 8548.8 | 0.34294618 | 9133.8 | 56628. | 0.02620577 |
| 69 | Ptgs2 | 161.9 | 78.1 | 0.35338939 | 3531.3 | 527.1 | 0.12463110 |
| 70 | Ptpn11 | 10079 | 75971. | 0.66679437 | 4499.0 | 12054 | 0.31601568 |
| 71 | Ptpn4 | 9183.5 | 15232. | 0.39201627 | 60.5 | 2724.9 | 0.35420116 |
| 72 | Ptpn9 | 3616.0 | 2714.9 | 0.68421590 | 484.1 | 124.3 | 0.69859351 |
| 73 | Rela | 3569.9 | 4952.7 | 0.38201894 | 6141.0 | 18723 | 0.32189398 |
| 74 | Selp | 280.0 | 38.3 | 0.17974904 | 1350.0 | 219.7 | 0.53174658 |
| 75 | Skil | 3194.8 | 2955.1 | 0.81270529 | 5065.5 | 6118.7 | 0.35055202 |
| 76 | Smad7 | 3138.8 | 2713.3 | 0.67047101 | 3259.6 | 3993.0 | 0.17786155 |
| 77 | Socs1 | 788.3 | 533.3 | 0.41163351 | 2788.9 | 776.5 | 0.34941798 |
| 78 | Socs4 | 1289.6 | 1490.1 | 0.93268357 | 32.3 | 3821.0 | 0.08597603 |
| 79 | Socs5 | 10969. | 7887.4 | 0.59069118 | 22396. | 992.4 | 0.05082208 |
| 80 | Stat3 | 8584.4 | 12035. | 0.50685499 | 467.1 | 32294. | 0.13197306 |
| 81 | Tbxa2 | 3379.7 | 3350.1 | 0.98484138 | 3674.9 | 1624.2 | 0.32129208 |
| 82 | Tbxas | 439.4 | 388.7 | 0.77614173 | 3585.0 | 2244.2 | 0.00461596 |
| 83 | Tfrc | 80675. | 35059. | 0.04584594 | 12281. | 852.9 | 0.28133811 |
| 84 | Tgfb1 | 5102.0 | 4333.5 | 0.58427727 | 9657.9 | 10129. | 0.76269059 |
| 85 | Tnf | 107.3 | 83.7 | 0.50278727 | 257.2 | 145.1 | 0.04438075 |
| 86 | Tnfrsf | 2346.8 | 1865.1 | 0.93077518 | 57.9 | 708.3 | 0.21259566 |
| 87 | Tnfsrf | 1258.9 | 1178.4 | 0.85124462 | 2598.6 | 2556.6 | 0.94198874 |
| 88 | Tnfsf1 | 27.9 | 22.3 | 0.60720401 | 53.9 | 60.9 | 0.64785196 |
| 89 | Traf2 | 857.9 | 761.0 | 0.73252703 | 2078.4 | 1289.2 | 0.02796907 |

TABLE 5-continued

Expression levels of immune response genes in miR142- or NT-transduced (control) wt and p300tg mouse hearts at 2 months. Shading = nominally significant (p <0.05) differential regulation by miR-142 in either or both wt and p300tg mice. n = 3 per condition.

| 90 | Traf3i | 953.8 | 953.4 | 0.99905890 | 1280.1 | 941.1 | 0.13690539 |
|---|---|---|---|---|---|---|---|
| 91 | Traf3 | 675.0 | 661.1 | 0.94903350 | 1200.6 | 971.8 | 0.63454391 |
| 92 | Traf6 | 595.8 | 507.1 | 0.65830884 | 859.6 | 726.8 | 0.28932474 |
| 93 | Trafd1 | 9773.5 | 10412. | 0.86784198 | 16268. | 12020. | 0.18192742 |
| 94 | Vcam | 1295.2 | 1956.0 | 0.29674550 | 2749.6 | 3167.2 | 0.52801827 |
| 95 | Vegfa | 38382. | 32287. | 0.61432611 | 64068. | 38351. | 0.09685446 |

TABLE 6

Functional alterations induced by restoration of miR-142 expression in mice. Echocardiographic parameters were assessed as in Methods in wt and p300tg littermate mice, 2 months after transduction of lentivirus expressing pri-miR-142 (miR-142) or a non-targeting control sequence (control).

| Echo parameters | Wild type | | p value (wt, ctrl vs. mir142) | p300tg | | p value (tg, ctrl vs mir142) |
|---|---|---|---|---|---|---|
| | Control (n = 8) | miR-142 (n = 7) | | Control (n = 5) | miR-142 (n = 5) | |
| Septal thickness (diastole) (mm) | 0.67 ± 0.05 | 0.54 ± 0.03 | 0.0463 | 0.56 ± 0.12 | 0.55 ± 0.07 | 0.8264 |
| Septal thickness (systole) (mm) | 0.88 ± 0.06 | 0.64 ± 0.02 | 0.0023 | 0.72 ± 0.12 | 0.65 ± 0.07 | 0.3190 |
| Cardiac output (ml) | 13.92 ± 1.47 | 11.44 ± 1.01 | 0.1998 | 13.31 ± 2.01 | 11.73 ± 1.52 | 0.1985 |
| LV internal dimension (diastole) (mm) | 3.53 ± 0.15 | 3.67 ± 0.07 | 0.4249 | 3.77 ± 0.17 | 4.13 ± 0.38 | 0.0864 |
| LV internal dimension (systole) (mm) | 1.99 ± 0.15 | 2.50 ± 0.11 | 0.0187 | 2.31 ± 0.20 | 3.20 ± 0.56 | 0.0105 |
| LV Ejection Fraction (%) | 75.82 ± 2.13 | 60.90 ± 2.49 | 0.0005 | 69.70 ± 4.26 | 45.96 ± 12.38 | 0.0037 |
| LV Fractional Shortening (%) | 44.00 ± 1.82 | 32.13 ± 1.77 | 0.0005 | 38.69 ± 3.24 | 22.97 ± 7.13 | 0.0020 |
| LV Stroke volume (%) | 39.46 ± 3.12 | 34.55 ± 0.50 | 0.1710 | 42.23 ± 3.47 | 33.70 ± 5.67 | 0.0208 |
| LV Volume (diastole) (ul) | 53.01 ± 5.71 | 57.34 ± 2.61 | 0.5232 | 60.78 ± 6.29 | 76.23 ± 16.18 | 0.0818 |
| LV Volume (systole) (ul) | 13.56 ± 2.72 | 22.78 ± 2.37 | 0.0256 | 18.55 ± 4.19 | 42.53 ± 17.46 | 0.0174 |
| LV posterior wall thickness (diastole) (mm) | 0.67 ± 0.05 | 0.65 ± 0.03 | 0.7515 | 0.76 ± 0.06 | 0.65 ± 0.06 | 0.0190 |
| LV posterior wall thickness (systole) (mm) | 1.11 ± 0.07 | 0.92 ± 0.03 | 0.0446 | 1.10 ± 0.19 | 0.78 ± 0.15 | 0.0162 |

Methods

Antibodies against p300 and GAPDH were from Santa Cruz Biotechnology, Santa Cruz Calif.; pan-α-actinin antibody from Sigma-Aldrich; Gata4 antibody from Abcam PLC, Cambridge, Mass.; sarcomeric myosin heavy chain MF20 antibody from the Developmental Studies Hybridoma Bank, University of Iowa; Alexa 555, Alexa 647 and Cy5 fluorophore-conjugated secondary antibodies from Molecular Probes. Rhodomine phalloidin and DAPI stains were from Invitrogen Corp., Carlsbad Calif. Inducible p300 recombinant adenovirus and QuickTiter Lentivirus titer kits were purchased from Cell Biolabs Inc., San Diego, Calif. siRNA directed against p300 was obtained from Thermo Fisher Scientific/Dharmacon RNAi Technologies, Lafayette, Colo. For chemiluminescence the Amersham ECL Western Detection System was used, from GE Healthcare Bio-Sciences. Lentiviruses for microRNA transduction were from Open Biosystems Products Inc., Huntsville Ala. LNA (Locked Nucleic Acid) oligonucleotides for knockdown of miR-142 (-5p and -3p) were obtained from Exiqon, Woburn, Mass. RNA and protein extractions used the mirVana miRNA Isolation Kit and mirVana Paris Kit from Applied Biosystems/Ambion, Austin Tex. Luciferase vectors containing selected 3' UTRs were obtained from GeneCopoeia, Rockville Md. Quick-Change Site-directed mutagenesis kits were purchased from Agilent/Stratagene, Santa Clara, Calif. Reagents for realtime quantitative PCR were obtained from Applied Biosystems, Carlsbad, Calif., including microRNA specific probes, transcript specific probes, Universal PCR Master Mix, MicroRNA Reverse Transcription kit, and High Capacity cDNA Reverse Transcription kit. TUNEL assay for apoptosis was performed using the CardioTACs kit from Trevigen, Gaithersburg, Md.

Methods for primary culture of neonatal rat cardiac myocytes have been previously described (Bishopric, N. H. & Kedes, L. Proc. Natl. Acad. Sci. USA 88, 2132-2136 (1991)). The final myocyte cultures contained >90% quiescent cardiac myocytes at partial confluence; 0.1 mmol/L bromodeoxyuridine was included in the medium for the first 3 days after plating to inhibit fibroblast growth.

Neonatal rat cardiac myocytes were cultured for 3 days in complete MEM media and 1% Brdu. Cells were serum-starved overnight with TIB (MEM supplemented with transferrin, vitamin B 12, insulin) media followed by p300 adenovirus transfection with at an MOI of 50 for overexpression or siRNA for p300 knock down. p300 overexpression or knock down was assessed following transfection by immunoblot. Overexpression of miRs was done using lentivirus transfections at an MOI of 2 and knock down was done using Locked Nucleic Acids at a concentration of 40 nM. MicroRNA levels were assessed 48 hour post transfection by qPCR. In cell staining, miR-142-5p knock down was achieved using lentiviral miR inhibitor (Genecoepia) at an MOI of 50.

For gene expression, cycling parameters were: 2 minutes at 50° C., 20 seconds at 95° C., 40 cycles: 1 second at 95° C. and 20 seconds at 60° C. Data was analyzed using the RQ Manager 1.2 from Applied Biosystems, CA. For microRNA quantitation, cycling parameters were: 2 minutes at 50° C., 10 minutes at 95° C., 40 cycles: 15 seconds at 95° C. and 1 minute at 60° C.

The cell lysate fractions were subjected to SDS-PAGE and transferred to nitrocellulose. Membranes were blocked for 1 hour at room temperature in 5% nonfat milk in a buffer containing (Tris 20 mM, sodium chloride 137 mM, 0.5% Tween-20 pH 7.5 (TBS-T)) and then incubated for 1 hour at room temperature with primary antibodies: followed by incubation for 45 minutes with horseradish peroxidase-conjugated secondary antibody. Proteins were imaged by chemiluminescence.

Nitrite level was used as an index of nitric oxide production. Nitrite levels were spectrophotometrically quantified cardiac myocyte cell culture media, with Griess reagent (Molecular Probes). The absorbance was read at 548 nm. The nitrite concentration was calculated with a sodium nitrite standard.

Mice were anesthetized and sacrificed by cervical dislocation at 2 and half months. Total heart weight, liver, lung, spleen, kidney weight and right tibia length were determined. Left ventricles were fixed in 5% paraformaldehyde in PBS and embedded in paraffin for hematoxylin and eosin (HE) staining. Paraffin embedded left ventricle sections were examined for apoptotic cardiomyocytes using a commercially available kit (Cardio-TACS, Trevigen) according to the manufacturer's instructions.

Fluorescent images of immunostaining were acquired on Olympus FV1000 confocal microscope and processed using FluoView10ASW (Olympus). Figure panels were assembled using Adobe Illustrator CS3.

All luciferase assays were performed on cos7 cells stable expressing control or miRs. 48 hours post-transfection, cell extracts were assayed for luciferase activity using the Luc-Pair miR luciferase assay kit (Genecoepia). Relative reporter activities are expressed as luminescence units normalized to Renilla luciferase activity in the cell extracts. Luminescence was quantitated using a multimode microplate reader (BMG Labtech).

Newborn (5 day) wt and p300tg pups received $8 \times 10^8$ viral particles of lentivirus expressing miR-142 or a control sequence via external jugular vein injection using a previously described method, with minor modifications (Kienstra et al., J Am Assoc Lab Anim Sci 46, 50-54 (2007)). In brief, 5 day old wt mouse pups and littermates with myocyte-specific overexpression of p300 (BS line) were placed on a transilluminator and the external jugular vein was injected with $8 \times 10^8$ viral particles of miR-142 or control. Injected pups were returned to their mothers until weaning at 3 weeks of age.

Rat Gene Expression microarray analysis was performed using non-Affymetrix single channel arrays (Ocean Ridge Biosciences). Microarray data has been submitted to GEO.

Microarray and low density TaqMan array expression ratios were calculated as the power-2 exponential of the log 2 differences. The acceptance criteria for gene array expression changes was a minimum 1.7 fold change and a one-way Analysis of Variance (ANOVA) t-test p-value of <0.05. In all cases, the acceptance level of significance was p<0.05 using a two-tailed distribution. Data analysis and hierarchical clustering were performed using XLSTAT. A custom heatmap display program was created in the R software environment.

Example 3 p300 Regulates Cardiac Myocyte Growth Through MIR374-5p

In the experiments described below, the hypothesis that p300 regulates hypertrophy by controlling the expression of specific microRNAs was tested. Transcription analysis revealed downregulation of the microRNA miR-374-5p (374) in p300 transgenic mouse left ventricles vs. wild-type littermates at various age groups. Induction of p300 was associated with downregulation of miR374 in both fetal bovine serum (FBS)-induced hypertrophy of neonatal rat myocytes (NRVM) in culture and following transverse aortic coarctation in vivo. Interestingly, miR374 is upregulated by inhibiting various growth factor-regulated MAPK signaling pathways, further confirming that hypertrophic program downregulates these microRNAs. miR374 is also repressed in human hearts with various types of cardiomyopathy Adenovirus-mediated overexpression of p300 in NRVM caused robust downregulation of miR374. Conversely, siRNA-mediated knockdown of p300 upregulated both microRNAs, suggesting that p300 is both necessary and sufficient to drive their expression. NRVM were transfected with lentiviral vectors expressing miR374 and stimulated with FBS. Strikingly, miR374-5p completely blocked the hypertrophic response to FBS. Gain and loss of expression of miR374 was associated with parallel changes in EGR4, a growth-associated transcriptional repressor. At the same time, gain and loss of miR374 expression caused reciprocal changes in HMGB2, a transcriptional activator upregulated in several types of cardiomyopathy. Furthermore, miR374 inhibits the expression of p300 transcriptional co-activator as a part of a negative feed back loop, suggesting a broad role of these microRNAs in regulating hypertrophy. These findings indicate that hypertrophic signals directly or indirectly repress miR374 that blocks critical aspects of hypertrophic adaptation by directly targeting the expression of p300 and indirectly targeting a group of early growth response proteins (EGRs).

Results miR374 is expressed and dynamically regulated during cardiac growth in vivo. An initial analysis of left ventricular myocardium comparing a-MHC-p300 transgenic mice and their wild type littermates indicated differential regulation of a small set of microRNAs, including miR374. In both p300tg and wt mice, miR374 levels were relatively low in the period of adaptive cardiac growth between birth and adulthood at 2 months, rising sharply at 3 months, then returning to baseline by 5 months. Even at 3 months, miR374 expression was very low compared to those of the highly abundant species miR-1 and miR-let-7c. Levels of miR374 were inversely regulated with p300 in various hypertrophy models: miR374 was significantly lower in p300-overexpressing myocardium at most time points, in wt mouse hearts following acute surgically induced pressure overload at early and late time points, and in human hearts with various types of cardiomyopathy, where p300 is also upregulated.

miR374 is downregulated during the onset of cardiac hypertrophy. The kinetics of miR374 repression by growth signals was examined, using a model of serum-induced cardiac myocyte hypertrophy in culture. 5% fetal calf serum (FCS) induced robust hypertrophy of neonatal rat cardiac myocytes, accompanied by a large rise in p300 levels within 2 hours that persisted for at least 36 hours. Over the same interval, miR374 showed a biphasic regulation with robust downregulation at 4 hours and significant but modest upregulation until 24 hours. Suppression was specific to miR374, as the unrelated microRNA miR-20a was upregulated throughout under the same conditions.

Growth factor-induced repression of miR374 is reversed by multiple MAP kinase inhibitors. Serum contains a mixture of growth factors that signal through one or more mitogen-activated protein kinase (MAPK) cascades, culminating in activation of the terminal effectors p38 MAPK, c-jun N-terminal kinases (JNKs) and p42/44 extracellular signal-regulated kinases (ERKs). The downstream phosphorylation of specific intracellular targets results in modulation of cardiac gene expression as a part of the hypertrophic response. To interrogate the role of MAPK signaling in repression of miR374, cardiac myocytes were stimulated with serum in the presence of well-characterized inhibitors of MEK1 (UO126), p42/p44 MAPK/ERK (PD98059) p38MAPK (SB202190) or c-Jun N-terminal kinase (JNK, SP600125) using concentrations previously shown to be at least partially selective for their respective targets. Treatment with any of these compounds reversed the serum-induced downregulation of miR374. These results indicate that miR374 is negatively regulated by serum growth factors, acting either through a combination of MAP kinases, or possibly through a single kinase that is inhibited by all 4 compounds.

Repression of miR374 by p300. Both ERK/MAPK and p38MAPK have been reported to phosphorylate and modulate the activity of p300. To determine whether p300 directly regulates miR374, cardiac myocytes were transduced with an adenovirus expressing full-length human p300 (Ad-p300), or transfected them with an anti-p300 silencing RNA (siRNA). Ad-p300, but not a blank Ad-GFP virus, significantly increased protein levels of p300 at both 48 hours and 72 hours, accompanied by a reduction in miR374. Conversely, cardiac myocytes transfected with anti-p300 siRNA but not with a non-silencing sequence (ns) had >70% reduction in p300 levels at both 48 hours and 72 hours, and this was accompanied by more than doubling of miR374 expression. Thus, p300 is both necessary and sufficient to drive the repression of miR374 in the absence of hypertrophic extracellular signals or MAPK activation.

MiR374 directly targets p300. A query using the TargetScan microRNA target prediction algorithm revealed a predicted binding site for miR374 in the p300 3'UTR, suggesting that miR374 might reciprocally inhibit p300. To investigate this, cardiac myocytes were transfected with lentiviral vectors encoding miR374 or a non-targeting scrambled sequence (NT). miR374 was expressed from the miR374 lentivirus, accompanied by a marked decrease in p300 protein levels. A luciferase expression vector containing the wild type p300 3'UTR was efficiently repressed by miR374. Mutation of the predicted miR374 binding site eliminated this repression, confirming a direct repression of p300 by miR374.

MiR374 induces and target genes involved in growth. It has been established that microRNAs have the ability to target a number of genes directly and as a consequence, may indirectly up-regulate or down-regulate a variety of genes downstream. In order to get a full picture of this broad effect of miR374, the microarray gene expression approach was followed. Using lentivirus, miR374-5p was over-expressed in cardiac myocytes followed with Gene expression microarray. Interestingly, it was found that a gain of miR374 causes up-regulation of early growth response proteins EGR1, EGR2 and EGR4. A number of studies implicate EGR proteins in the regulation of proinflammatory cytokine gene expression. In addition, gain and loss of miR374 expression was associated with parallel changes in EGR4, which is also a growth-associated transcriptional repressor. At the same time, gain and loss of miR374 expression caused reciprocal changes in HMGB2. HMGB2 is a non-histone chromatin-associated transcriptional activator in mammals. HMGB2 functions in a number of fundamental cellular processes such as transcription, replication, DNA repair and recombination. It is up regulated in several types of cardiomyopathy. Collectively, this data suggests that miR374 play an essential role in modulating a number of physiologic processes including growth and thus, appear to play a key role in cardiac remodeling.

miR374 blocks serum-induced hypertrophy in cardiac myocytes. Serum is one of the most potent hypertrophic stimuli. Serum induction results in increase in cell size and protein content in neonatal cardiac myocytes. In order to assess the physiological relevance of miR374 in cardiac myocytes in the context of hypertrophy, miR374 was overexpressed using a GFP-tagged lentiviral construct in neonatal cardiac myocytes and they were stimulated with serum. Strikingly, miR374-5p completely blocked the hypertrophic response to FBS compared to control cells inhibition of miR374-5p has no apparent effect on the size of serum stimulated cardiac myocytes.

Experimental Procedures

Antibodies against p300 and GAPDH were from Santa Cruz Biotechnology, Santa Cruz Calif.; Gata4 antibody from Abcam PLC, Cambridge, Mass.; sarcomeric myosin heavy chain MF20 antibody from the Developmental Studies Hybridoma Bank, University of Iowa; Alexa 555, Alexa 647 and Cy5 fluorophore-conjugated secondary antibodies from Molecular Probes. Rhodomine phalloidin and DAPI stains were from Invitrogen Corp., Carlsbad Calif. Inducible p300 Recombinant Adenovirus and QuickTiter Lentivirus Titer kits were purchased from Cell Biolabs Inc., San Diego, Calif. siRNA directed against p300 was obtained from Thermo Fisher Scientific/Dharmacon RNAi Technologies, Lafayette, Colo. For chemiluminescence we used the Amersham ECL Western Detection System, GE Healthcare Bio-Sciences. Lentiviruses for microRNA transduction were from Open Biosystems Products Inc., Huntsville Ala. LNA (Locked Nucleic Acid) oligonucleotides for knockdown of miR374 were obtained from Exiqon, Woburn, Mass. RNA and protein extractions used the mirVana miRNA Isolation Kit and mirVana Paris Kit from Applied Biosystems/Ambion, Austin Tex. Luciferase vectors containing selected 3' UTRs were obtained from GeneCopoeia, Rockville Md. QuickChange Site-directed mutagenesis kits were purchased from Agilent/Stratagene, Santa Clara, Calif. Reagents for realtime quantitative PCR were obtained from Applied Biosystems, Carlsbad, Calif., including microRNA specific probes, transcript specific probes, Universal PCR Master Mix, MicroRNA Reverse Transcription kit, and High Capacity cDNA Reverse Transcription kit.

Methods for primary culture of neonatal rat cardiac myocytes have been previously described. The final myocyte cultures contained >90% quiescent cardiac myocytes at partial confluence; 0.1 mmol/L bromodeoxyuridine was included in the medium for the first 3 days after plating to inhibit fibroblast growth.

The cell lysate fractions were subjected to SDS-PAGE and transferred to nitrocellulose. Membranes were blocked for 1 hour at room temperature in 5% nonfat milk in a buffer containing (Tris 20 mM, sodium chloride 137 mM, 0.5% Tween-20 pH 7.5 (TBS-T)) and then incubated for 1 hour at room temperature with primary antibodies: followed by incubation for 45 minutes with horseradish peroxidase-conjugated secondary antibody. Proteins were imaged by chemiluminescence.

Neonatal rat cardiac myocytes were cultured for 3 days in complete MEM media and 1% Brdu. Cells were serum-starved overnight with TIB (MEM supplemented with transferrin, vitamin B 12, insulin) media followed by p300 adenovirus transfection with at an MOI of 50 for overexpression or siRNA for p300 knock down. p300 overexpression or knock down was assessed following transfection by immunoblot. Overexpression of miRs was done using lentivirus transfections at an MOI of 2 and knock down was done using Locked Nucleic Acids at a concentration of 40 nM. MicroRNA levels were assessed 48 hour post transfection by qPCR. In cell staining, miR-142-5p knock down was achieved using lentiviral miR inhibitor (Genecoepia) at an MOI of 50.

Fluorescent images of immunostaining were acquired on Olympus FV1000 confocal microscope and processed using FluoView10ASW (Olympus).

Rat Gene Expression Microarray Analysis was performed by Ocean Ridge Biosciences. Microarray data is being submitted to GEO.

For gene expression, cycling parameters were: 2 minutes at 50° C., 20 seconds at 95° C., 40 cycles: 1 second at 95° C. and 20 seconds at 60° C. Data was analyzed using the RQ Manager 1.2 from applied Biosystems, CA. For microRNA quantitation, cycling parameters were: 2 minutes at 50° C., 10 minutes at 95° C., 40 cycles: 15 seconds at 95° C. and 1 minute at 60° C.

All luciferase assays were performed on cos7 cells stable expressing control or miRs. 48 hours post-transfection, cell extracts were assayed for luciferase activity using the Luc-Pair miR luciferase assay kit (Genecoepia). Relative reporter activities are expressed as luminescence units normalized to Renilla luciferase activity in the cell extracts. Luminescence was quantitated using a multimode microplate reader (BMG Labtech).

Microarray and low density TaqMan array expression ratios were calculated as the power-2 exponential of the log 2 differences. The acceptance criteria for gene array expression changes was a minimum 1.7 fold change and a one-way Analysis of Variance (ANOVA) t-test p-value of <0.05. In all cases, the acceptance level of significance was p<0.05 using a two-tailed distribution. Data analysis and hierarchical clustering were performed using XLSTAT. A custom heatmap display program was created in the R software environment.

The results described herein have identified a novel role for miR374 in the context of cardiac growth and hypertrophy. First, it was observed that miR374 was regulated in the p300 transgenic model of cardiac hypertrophy. In addition, miR374 regulation was validated both in vitro and in an in vivo physiological hypertrophy model. Second, it was shown that miR374 has a dynamic temporal expression pattern and can target p300 inversely and is reciprocally regulated by p300 level in vitro. Third, it was found that miR374 indirectly targets a group of early growth response proteins (EGRs) and myocytes overexpressing miR374 were completely resistant to hypertrophic stimulation by fetal bovine serum. It can be concluded that miR374 negatively regulates hypertrophy through direct effects on p300 and indirect effects on early growth response proteins and transcriptional repressor HMGB2.

These findings have important clinical implications. In summary, an important microRNA has been identified that is repressed and regulated by p300. More importantly, by targeting a nodal and master regulator of transcription p300, miR374 seems to play a key role in cardiac growth. This dynamic equilibrium between p300 and miR374 seems to regulate cardiac homeostatis. Deregulation of this equilibrium may have adverse effect on cardiac growth and remodeling.

OTHER EMBODIMENTS

Any improvement may be made in part or all of the compositions, cells, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method of treating heart failure and arterial obstructive disease in a subject comprising administering to the subject a composition comprising: a pharmaceutically acceptable carrier and at least one of: an agent that down regulates activity or expression of miR-142-5p in an amount sufficient to promote cardiac cell survival and enhance cardiac function in the subject, and an agent that upregulates miR-374 activity or expression in an amount sufficient to prevent myocyte hypertrophy in the subject,
wherein the agent that downregulates activity or expression of miR-142-5p is an antisense molecule having complementarity to the precursor or mature sequence of miR-142-5p, and the agent that upregulates miR-374 activity or expression is a nucleic acid encoding a precursor or mature sequence of miR-374.

2. A method for treating an inflammatory or immunological disorder involving a subject's cardiovascular system comprising administering to the subject a composition comprising a pharmaceutically acceptable carrier and at least one agent that increases activity or expression of at least one of: miR-142-5p and/or miR-142-3p, in an amount effective for repressing inflammatory cytokine gene expression and alleviating or treating the inflammatory or immunological disorder in the subject,
wherein the at least one agent that increases activity or expression of at least one of: miR-142-5p and/or miR-142-3p is a nucleic acid encoding a precursor form of miR-142-5p or a precursor form of miR-142-3p.

3. The method of claim 2, wherein the inflammatory or immunological disorder involving a subject's cardiovascular system is selected from the group consisting of: atherosclerosis, vasculitis, lupus erythematosus, sclerodema, rheumatoid arthritis, cardiac transplant rejection, adult respiratory distress syndrome, and any condition in which autoantibodies are produced.

* * * * *

UNITED STATES PATENT AND TRADEMARK OFFICE
CERTIFICATE OF CORRECTION

| | | |
|---|---|---|
| PATENT NO. | : 9,248,144 B2 | Page 1 of 1 |
| APPLICATION NO. | : 13/884060 | |
| DATED | : February 2, 2016 | |
| INVENTOR(S) | : Nanette Bishopric et al. | |

It is certified that error appears in the above-identified patent and that said Letters Patent is hereby corrected as shown below:

On title page 1, column 1, under item (75) Inventors: Nanette Bishopric, Coral Gables, FL (US); Jing Liu, Miami, FL (US); Salil Sharma, Miami, FL (US) should read -- Nanette Bishopric, Coral Gables, FL (US); Salil Sharma, Miami, FL (US) --

Signed and Sealed this
Tenth Day of May, 2016

Michelle K. Lee
*Director of the United States Patent and Trademark Office*